United States Patent [19]

Pierce et al.

[11] Patent Number: 5,602,003
[45] Date of Patent: Feb. 11, 1997

[54] N-ACETYLGLUCOSAMINYLTRANSFERASE V GENE

[75] Inventors: J. Michael Pierce, Athens; Mohamed G. Shoreibah, Comer, both of Ga.; Beverly S. Adler, Newbury Park, Calif.; Nevis L. Fregien, Miami, Fla.

[73] Assignee: University of Georgia Research Foundation, Athens, Ga.

[21] Appl. No.: 16,863

[22] Filed: Feb. 10, 1993

Related U.S. Application Data

[63] Continuation-in-part of Ser. No. 905,795, Jun. 29, 1992, abandoned.

[51] Int. Cl.$^6$ .............................. C07H 21/04; C12N 5/10
[52] U.S. Cl. .................. 435/69.1; 435/70.1; 435/252.3; 435/252.33; 435/193; 435/320.1; 435/365; 435/325; 536/23.2; 536/23.5
[58] Field of Search ................... 435/69.1, 70.1, 435/240.2, 252.3, 252.33, 320.1, 193, 71.1, 71.2; 536/23.2, 23.5

[56] References Cited

PUBLICATIONS

Saito et al., *Bioch. Biophys. Res. Comm.* 198(1), 318–327 (1994).
Miyoshi et al., *Cancer Res.* 53, 3899–3902 (Sep. 1993).
Gu et al., *J. Biochem.* 113, 614–619 (1993).
Fregian et al., *FASEB J.* 4(7), A 1979 (1990).
Lee et al., *Science* 239, 1288–1291 (1988).
Shoreibah et al. (1992) *J. Biol. Chem* 267:2920–2927.
Shoreibah et al. (1991) *Glycoconjugate J.* 8:260.
Palcic et al. (1990) *J. Biol. Chem.* 265:6759–6769.
Pierce et al. (1987) *Biochem. Biophys. Res. Commun.* 146:679–684.
Bendiak et al. (1987) *J. Biol. Chem.* 262(12):5784–5790.
Oppenheimer et al. (1981) *J. Biol. Chem.* 256(2):799–804.
Frohman et al. (1988) *Proc. Natl. Acad. Sci. USA* 85:8998–9002.
Larsen et al. (1989) *Proc. Natl. Acad. Sci. USA* 86:8227–8231.
Pierce et al. (1990) *J. Cell Biol.* 111(5): Part 2. (Abstract).
Moreman et al. (1991) *J. Cell. Biol.* 115:1521–1534.
Weinstein et al. (1987) *J. Biol. Chem.* 262:17735–17743.
Colley et al. (1989) *J. Biol. Chem.* 264:17619–17622.
Larsen et al. (1990) *Proc. Natl. Acad. Sci. USA* 87:6674–6678.
Barker et al. (1972) *J. Biol. Chem.* 247:7135–7147.
Pinto et al. (1983) *Carbohydr. Res.* 124:313–318.
Wen et al. (1992) *Cell* 69:559–572.

*Primary Examiner*—W. Gary Jones
*Assistant Examiner*—Kenneth R. Horlick
*Attorney, Agent, or Firm*— Greenlee and Winner

[57] ABSTRACT

The present invention provides a substantially purified UDP-N-acetylglucosamine:$\alpha$-6-D-mannoside $\beta$-1,6-N-acetylglucosaminyltransferase (GlcNAc T-V; EC 2.4.1.155) and antibodies which specifically bind GlcNAc T-V. The present invention also provides polynucleotide sequences and oligonucleotide probes capable of specifically hybridizing to nucleic acid sequences which encode GlcNAc T-V, and cDNA and genomic clones encoding GlcNAc T-V, as well as nucleotide sequences encoding GlcNAc T-V, as specifically exemplified by a GlcNAc T-V coding sequence from rat.

13 Claims, 15 Drawing Sheets

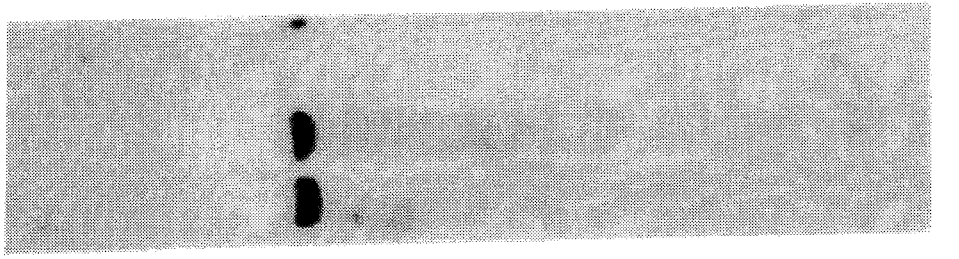
FIG.5D
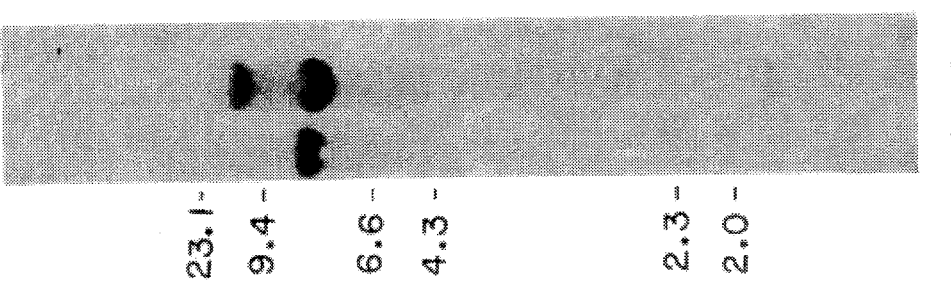
FIG.5C
FIG.5B
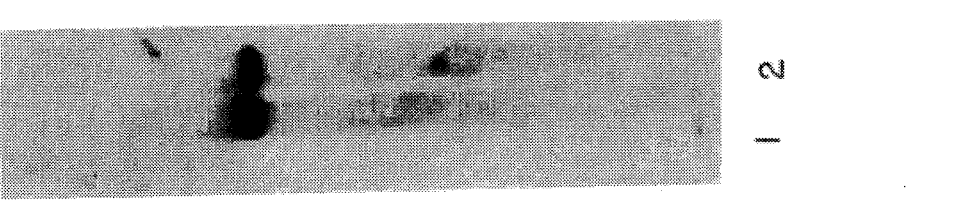
FIG.5A
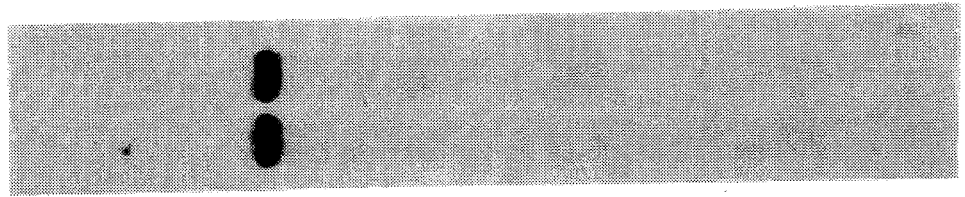

|  |  |
|---|---|
| T | |
| GACCCCGCTCCTGGCTGTGCCTGGGACCCCAGTTCCCAGGAGCACGGTTGCAGGAGAGTG | 61 |
| ACCCCGACTGCTACTGATGGTGCTTCTGCTGCTCCTCTACTAGCAGGAGTGACTCCTACC | 121 |
| CAGAAGTGGACTTGGAGGAGGGTCCGTTAGACCATCAGAATGGAAGCCCGACAAGCAAGT | 181 |
| CAGCTGACTCAGGAACCAGAGTGAGGGCCACGCACTCTCCGCCCCAGCCTGCACCATGAA | 241 |
| CTTGCCTTCCCCTTCTGCTTGTTGAGAGCCAAGGGAATGGTACATTACTAGAGAGAGATG | 301 |
|                                                      Met    |     |
|                                                        1    |     |

GCTTTCTTTTCTCCCTGGAAGTTGTCCTCTCAGAAGCTGGGCTTTTTCTTGGTGACTTTT     361
AlaPhePheSerProTrpLysLeuSerSerGlnLysLeuGlyPhePheLeuValThrPhe

GGCTTCATATGGGGGATGATGCTTCTACACTTCACCATCCAGCAGCGAACTCAGCCTGAG     421
GlyPheIleTrpGlyMetMetLeuLeuHisPheThrIleGlnGlnArgThrGlnProGlu

AGCAGCTCCATGTTGCGGGAGCAAATCCTTGACCTCAGCAAAAGGTACATTAAGGCACTG     481
SerSerSerMetLeuArgGluGlnIleLeuAspLeuSerLysArgTyrIleLysAlaLeu
                          50

GCAGAAGAGAACAGGAACGTGGTGGATGGCCCGTATGCCGGTGTCATGACAGCCTATGAT     541
AlaGluGluAsnArgAsnValValAspGlyProTyrAlaGlyValMetThrAlaTyrAsp

CTGAAGAAAACGCTCGCCGTGCTGCTGGATAACATCTTGCAGCGCATCGGCAAGCTGGAG     601
LeuLysLysThrLeuAlaValLeuLeuAspAsnIleLeuGlnArgIleGlyLysLeuGlu
                                                        100

TCCAAGGTGGACAATCTTGTCAACGGCACAGGAGCGAATTCTACCAACTCCACCACGGCT     661
SerLysValAspAsnLeuValAsnGlyThrGlyAlaAsnSerThrAsnSerThrThrAla
              *              *         *
             109            114       117

FIGURE 10B

```
GTCCCCAGCTTGGTGTCACTGGAGAAAATTAATGTGGCAGATATCATTAATGGAGTTCAA      721
ValProSerLeuValSerLeuGluLysIleAsnValAlaAspIleIleAsnGlyValGln

GAAAAATGTGTATTGCCTCCTATGGATGGCTACCCCCACTGCGAGGGGAAAATCAAGTGG      781
GluLysCysValLeuProProMetAspGlyTyrProHisCysGluGlyLysIleLysTrp
                            150

ATGAAAGACATGTGGCGGTCAGACCCCTGCTACGCAGACTATGGAGTGGACGGGACCTCC      841
MetLysAspMetTrpArgSerAspProCysTyrAlaAspTyrGlyValAspGlyThrSer

TGCTCCTTTTTTATTTACCTCAGTGAGGTTGAAAATTGGTGTCCTCGTTTACCTTGGAGA      901
CysSerPhePheIleTyrLeuSerGluValGluAsnTrpCysProArgLeuProTrpArg
                                                          200

GCAAAAAATCCCTATGAAGAAGCTGACCATAACTCATTGGCAGAAATCCGCACGGATTTT      961
AlaLysAsnProTyrGluGluAlaAspHisAsnSerLeuAlaGluIleArgThrAspPhe

AACATTCTCTACGGCATGATGAAGAAGCATGAGGAGTTCCGGTGGATGAGACTTCGGATC    1021
AsnIleLeuTyrGlyMetMetLysLysHisGluGluPheArgTrpMetArgLeuArgIle

CGGCGAATGGCTGATGCATGGATCCAAGCAATCAAGTCTCTGGCAGAGAAACAAAACCTA    1081
ArgArgMetAlaAspAlaTrpIleGlnAlaIleLysSerLeuAlaGluLysGlnAsnLeu
                            250

GAGAAGAGGAAACGGAAGAAAATCCTTGTTCACCTGGGGCTCCTGACCAAGGAATCAGGC    1141
GluLysArgLysArgLysLysIleLeuValHisLeuGlyLeuLeuThrLysGluSerGly

TTCAAGATTGCAGAGACAGCATTCAGCGGTGGCCCTCTCGGCGAGCTCGTTCAGTGGAGT    1201
PheLysIleAlaGluThrAlaPheSerGlyGlyProLeuGlyGluLeuValGlnTrpSer
                                                          300
```

FIGURE 10C

```
GACTTAATCACATCTCTGTACCTGCTGGGCCATGACATCCGCATCTCAGCCTCGCTGGCT      1261
AspLeuIleThrSerLeuTyrLeuLeuGlyHisAspIleArgIleSerAlaSerLeuAla

GAGCTCAAGGAGATTATGAAGAAGGTTGTTGGAAACCGGTCTGGCTGTCCAACTGTAGGA      1321
GluLeuLysGluIleMetLysLysValValGlyAsnArgSerGlyCysProThrValGly
                                *
                               333

GACAGAATCGTTGAGCTTATTTATATCGATATTGTGGGACTTGCTCAATTCAAGAAAACG      1381
AspArgIleValGluLeuIleTyrIleAspIleValGlyLeuAlaGlnPheLysLysThr

CTAGGACCATCCTGGGTTCATTACCAGTGCATGCTCCGGGTGCTGGACTCCTTTGGAACA      1441
LeuGlyProSerTrpValHisTyrGlnCysMetLeuArgValLeuAspSerPheGlyThr

GAACCTGAGTTCAATCACGCAAGTTACGCCCAGTCGAAAGGCCACAAGACCCCCTGGGGA      1501
GluProGluPheAsnHisAlaSerTyrAlaGlnSerLysGlyHisLysThrProTrpGly
                                                          400

AAGTGGAATCTGAACCCGCAACAGTTTTACACCATGTTCCCTCATACCCCAGACAACAGC      1561
LysTrpAsnLeuAsnProGlnGlnPheTyrThrMetPheProHisThrProAspAsnSer

TTTCTGGGCTTCGTGGTCGAGCAGCACCTGAACTCCAGCGACATCCACCACATTAACGAG      1621
PheLeuGlyPheValValGluGlnHisLeuAsnSerSerAspIleHisHisIleAsnGlu

ATCAAAAGGCAGAACCAGTCCCTTGTGTATGGCAAAGTGGATAGTTTCTGGAAGAATAAG      1681
IleLysArgGlnAsnGlnSerLeuValTyrGlyLysValAspSerPheTrpLysAsnLys
                *                 450
               440

AAGATCTACTTGGACATCATTCACACGTACATGGAAGTGCACGCCACTGTTTACGGCTCC      1741
LysIleTyrLeuAspIleIleHisThrTyrMetGluValHisAlaThrValTyrGlySer
```

FIGURE 10D

| | |
|---|---|
| AGTACCAAGAACATCCCCAGTTACGTGAAAAACCATGGCATTCTCAGCGGCCGTGACCTA<br>SerThrLysAsnIleProSerTyrValLysAsnHisGlyIleLeuSerGlyArgAspLeu<br>500 | 1801 |
| CAGTTTCTTCTCCGGGAAACCAAGCTTTTTGTTGGGCTTGGATTCCCTTATGAAGGTCCA<br>GlnPheLeuLeuArgGluThrLysLeuPheValGlyLeuGlyPheProTyrGluGlyPro | 1861 |
| GCTCCCCTGGAAGCCATCGCGAATGGATGTGCTTTCCTGAACCCCAAGTTCAACCCTCCT<br>AlaProLeuGluAlaIleAlaAsnGlyCysAlaPheLeuAsnProLysPheAsnProPro | 1921 |
| AAAAGCAGCAAAAACACAGACTTCTTCATTGGCAAGCCAACACTGAGAGAGCTCACATCC<br>LysSerSerLysAsnThrAspPhePheIleGlyLysProThrLeuArgGluLeuThrSer<br>550 | 1981 |
| CAGCACCCGTACGCAGAAGTCTTCATCGGCCGGCCACACGTCTGGACCGTGGACCTCAAT<br>GlnHisProTyrAlaGluValPheIleGlyArgProHisValTrpThrValAspLeuAsn | 2061 |
| AACCGAGAGGAAGTAGAAGACGCAGTAAAAGCCATCTTAAACCAGAAGATTGAGCCGTAT<br>AsnArgGluGluValGluAspAlaValLysAlaIleLeuAsnGlnLysIleGluProTyr | 2101 |
| ATGCCATATGAGTTCACATGTGAAGGCATGCTGCAGAGAATCAACGCTTTCATCGAGAAA<br>MetProTyrGluPheThrCysGluGlyMetLeuGlnArgIleAsnAlaPheIleGluLys | 2162 |
| CAGGACTTCTGCCACGGCCAAGTGATGTGGCCGCCCCTTAGCGCCCTGCAGGTGAAGCTG<br>GlnAspPheCysHisGlyGlnValMetTrpProProLeuSerAlaLeuGlnValLysLeu | 2221 |
| GCTGAGCCCGGGCAGTCCTGCAAACAGGTGTGCCAGGAGAGCCAGCTCATCTGCGAGCCG<br>AlaGluProGlyGlnSerCysLysGlnValCysGlnGluSerGlnLeuIleCysGluPro<br>650 | 2281 |
| TCCTTCTTCCAGCACCTCAACAAGGAAAAGGACCTGCTGAAGTATAAGGTAATCTGCCAA<br>SerPhePheGlnHisLeuAsnLysGluLysAspLeuLeuLysTyrLysValIleCysGln | 2341 |

FIGURE 10E

```
AGCTCAGAACTATACAAGGACATCCTGGTGCCCTCCTTCTACCCCAAGAGCAAGCACTGT      2401
SerSerGluLeuTyrLysAspIleLeuValProSerPheTyrProLysSerLysHisCys
                                                        700

GTGTTCCAAGGGGATCTCCTGCTCTTCAGTTGTGCCGGGGCCCACCCCACACACCAGCGG     2461
ValPheGlnGlyAspLeuLeuLeuPheSerCysAlaGlyAlaHisProThrHisGlnArg

ATCTGCCCCTGCCGGGACTTCATCAAGGGCCAAGTGGCCCTCTGCAAAGACTGCCTATAG    2521
IleCysProCysArgAspPheIleLysGlyGlnValAlaLeuCysLysAspCysLeuEnd

CATAGCCACCCTGGATTCATTCAGATGGGAAAGACGTGGCTCCGCTGGGCAGGGCCGAGG    2581

GGCTGAAAGACAGTCAGGGACTCTGACCAGAGCCTGAAATCTT
```

FIGURE 11

```
        1                                                            60
Mouse   AATACGGATTTCTTCATCGGGAAGCCTACACTGAGAGAGCTGACATCCCAGCATCCTTAC
        ::  :::::  ::  ::  ::::::::::::::::::::::::  ::::::::::::  :::
rat     AACACGGACTTTTTTATCGGGAAGCCTACACTGAGAGAGCTCACATCCCAGCACCCGTAC 61                                                          120
Mouse   GCAGAAGTCTTCATCGGCCGGCCACACGTCTGGACTGTGGACCTCAATAACCGAGAGGAA
        :::::::::::::::::::::::::::::::::::::  :::::  ::::::::::::::::
rat     GCAGAAGTCTTCATCGGCCGGCCACACGTCTGGACCGTGGACCTCAATAACCGAGAGGAA 121                                                         180
Mouse   GTAGAAGATGCAGTAAAAGCCATCTTAAACCAGAAGATTGAGCCCTATATGCCCTAC-G
        :::::::  :::::::::::::::::::::::  :::::  :::::  ::::::::::
rat     GTAGAAGACGCAGTAAAAGCCATCTTAAACCAAAAAAATTGAACCCTACATGCCCTACGA
```

5,602,003

N-ACETYLGLUCOSAMINYLTRANSFERASE V GENE

This application is a continuation-in-part of U.S. Ser. No. 07/905,795, filed Jun. 29, 1992, now abandoned.

FIELD OF THE INVENTION

The field of this invention is the area of protein glycosylation, specifically the area of the particular enzyme, UDP N-acetylglucosaminyltransferase V, involved in the expression of the β(1,6) branch structure found in tri- and tetraantennary N-linked oligosaccharides. The field relates to purified active enzyme, the amino acid sequence of the rat enzyme protein, genes encoding active enzyme and cell lines genetically engineered to express a nucleotide sequence encoding active enzyme.

BACKGROUND OF THE INVENTION

UDP-N-acetylglucosamine:α-6-D-mannoside β-1,6-N-acetylglucosaminyltransferase V (GlcNAc T-V; EC 2.4.1.155) is the Golgi enzyme responsible for the synthesis of the β(1,6) branch structure of tri- and tetraantennary N-linked oligosaccharides. For brevity, this enzyme is abbreviated GlcNAc T-V herein. GlcNAc T-V activity has been found in many mammalian tissues and cell types.

Altered glycosylation of membrane glycoproteins and glycolipids is observed in mammalian cells transformed with diverse tumor viruses, carcinogens, or transfection with certain oncogenes. In some cases, there is a quantitative increase in a particular substituent, e.g., sialylation. In other instances, there is the reappearance of an oligosaccharide structure in the tumor which is normally only found in fetal tissue; for instance, certain Lewis histo-blood group antigens have been detected in adenocarcinomas.

Qualitative differences in oligosaccharides may also be observed in certain transformed cells. BHK fibroblasts transformed with polyoma virus or with Rous sarcoma virus display more highly branched complex N-linked oligosaccharides than do the corresponding normal cells. The expression of the β-1,6 branch structure (-[GlcNAc-β(1,6)Man-α(1,6)Man]-) found in tri- and tetraantennary N-linked oligosaccharides is increased in the transformed cells. This has been correlated with a 2 to 3-fold increase in the specific activity of GlcNAc T-V. Transformation of murine cells with polyoma viruses, adenovirus, tumorigenic DNA and either the ras or the fps/fes oncogenes also resulted in increased GlcNAc T-V activity. By contrast, several other glycosyl transferases involved in N-linked glycosylation are unchanged in the transformed cells. The mechanism for the increased specific activity of GlcNAc T-V in transformed cells is not known.

The increase in the β(1,6) branching of the cell surface-bound oligosaccharides has been associated, at least in some cases, with capacity for metastasis. Increased levels of β-1,6 branching over the level in normal tissue has been observed for some human breast tumor tissues.

Certain mammalian glycosyltransferases from the N-linked glycosylation pathway have been purified and characterized. The enzymatic machinery for the glycosylation of proteins in mammalian cells is generally located in the membranes of the Golgi apparatus. α(1,3) mannoside β(1,2) UDP-N-acetylglucosaminyltransferase I (GlcNAc T-I) (EC 2.4.1 101) and UDP-N-acetylglucosaminyltransferase II (GlcNAc T-II) (EC 2.4.1.143) have been purified from rabbit liver and rat liver, respectively. GlcNAc T-I has been purified 7000-fold from a Triton X-100 extract of rabbit liver acetone powder by two rounds of affinity chromatography over UDP-hexanolamine agarose, in the first round by elution with NaCl, and in the second round by elution with UDP. The specific activity of the purified enzyme was 2.5 μmol/mg·min (Oppenheimer and Hill (1981) J. Biol. Chem. 256:799–804). GlcNAc T-II (UDP-N-acetylglucosaminyl:α-D-mannoside β(1,2) N-acetylglucosaminyltransferase II) was purified 60,000-fold from rat liver by Triton X-100 extraction of rat liver membranes, followed by chromatography over carboxymethyl-cellulose, hydroxylapatite, and sequential elutions using NaCl, UDP-GlcNAc and EDTA from 5-mercuri-UDP-GlcNAc-thiopropyl-SEPHAROSE, Affi-Gel (Bio-Rad Laboratories, Richmond, Calif.) blue affinity chromatography and finally UDP-GlcNAc-SEPHAROSE. The specific activity of the purified enzyme was 27.5 μmol/mg·min (Bendiak and Schachter (1987) J. Biol. Chem. 262:5775–5783).

The cDNA encoding a rat liver Golgi sialyltransferase (β-galactoside α(2,6)-sialyltransferase (EC 2.4.99.1) has been cloned and sequenced (Weinstein et al. (1987) J. Biol. Chem. 262:17735–17743). The corresponding enzyme has been purified 23,000-fold from Triton CF-54 extracts of rat liver membranes by three rounds of affinity chromatography over CDP-hexanolamineagarose. The specific activity of the purified enzyme was 8.2 μmol/mg·min (Weinstein et al. (1982) J. Biol. Chem. 257:13835–13844).

A portion of the work related to this invention has been published (Shoreibah et al. (1992) J. Biol. Chem. 267:2920–2927).

SUMMARY OF THE INVENTION

An object of this invention is a substantially pure N-acetylglucosaminyltransferase V enzyme. GlcNAc T-V can be substantially purified from a detergent (e.g., Triton X-100) extract of acetone-insoluble protein prepared from a biological material such as rat kidney by affinity chromatography over a solid support to which a substrate analog ligand is covalently linked, preferably UDP-hexanolamine-agarose, followed by affinity chromatography over an enzyme inhibitor of GlcNAc T-V (e.g., the oligosaccharide inhibitor disclosed herein) linked to a solid support via bovine serum albumin and a further purification step of affinity chromatography using a matrix to which a substrate analog ligand is attached, e.g., over UDP-hexanolamine-agarose. The substantially pure enzyme prepared from rat kidney has a specific activity of at least about 18 μmol/(min·mg) in the assay disclosed herein, and migrates as a doublet of 69 and 75 kDa on SDS-PAGE as described herein; only these two bands are visible by silver staining. The substantially pure GlcNAc T-V of this invention will be useful in in vitro enzymatic reactions of this enzyme.

Also embodied in the invention are genomic and cDNA sequences encoding glcNAc T-V, the amino acid sequences of GlcNAc T-V enzymes, and recombinant host cells genetically engineered to express a sequence encoding an active GlcNAc T-V enzyme.

Also provided by this invention are polyclonal and monoclonal antibodies specific for rat kidney GlcNAc T-V. These antibodies will also bind to and be useful for detection and isolation of GlcNAc T-V from other mammalian sources. It is understood that the molecular weight, kinetic parameters and primary amino acid sequence of GlcNAc T-V from a source other than rat kidney may vary from those values disclosed herein for the rat kidney enzyme.

Also provided in this invention is GlcNAc T-V produced by recombinant DNA technology in prokaryotic or eukaryotic host cells. Disclosed in this invention is the complete amino acid sequence for rat GlcNAc T-V and a complete nucleotide sequence encoding rat GlcNAc T-V. Examples of methods of producing recombinant active GlcNAc T-V by recombinant DNA technology are disclosed. The exemplified amino acid sequence and the nucleotide sequence encoding GlcNAc T-V, and subsequences within, as understood in the art, will be useful for isolating GlcNAc T-V coding sequences from a wide range of species and for producing useful quantities of GlcNAc T-V by recombinant DNA technology.

Further objects of this invention are cDNA clones encoding GlcNAc T-V and genomic clones encoding GlcNAc T-V. The antibodies raised against rat kidney GlcNAc T-V can be used to detect expression of GlcNAc T-V from sources other than rat kidney by virtue of cross-reactivity with those other GlcNAc T-V enzymes; alternatively, these antibodies can be used to screen cDNA expression libraries. Similarly, the degenerate oligonucleotide probes and/or the coding sequence and/or the amplimer sequences of the present invention can be used to screen genomic or cDNA libraries constructed using nucleic acids from mammalian sources other than rat kidney, or these can be used to prepare primers to amplify sequences encoding GlcNAc T-V from mRNA populations prepared from rat kidney or from other mammalian sources. The cDNA and/or genomic sequences encoding GlcNAc T-V will be useful in directing the recombinant expression of GlcNAc T-V.

Further objects of this invention are nucleotide sequences encoding rat GlcNAc T-V, and nucleotide sequences encoding GlcNAc T-V from other vertebrate, preferably mammalian, sources, including cDNA and genomic sequences. The nucleotide sequence encoding rat GlcNac T-V is provided herein as SEQ ID NO:15, from an ATG translation start codon beginning at nucleotide 299 through a translation stop codon ending at nucleotide 2521. The skilled artisan recognizes that there will be more than one nucleotide sequence capable of encoding the same amino acid sequence due to the degeneracy of the genetic code. These sequences, and sequence variants thereof which encode functionally equivalent GlcNAc T-V, can be used to express GlcNAc T-V in a desired recombinant host cell. The GlcNAc T-V coding sequences from other vertebrate species, preferably from mammals, will be highly homologous at the nucleotide sequence level to the exemplified rat GlcNAc T-V coding sequence disclosed herein. Functionally equivalent GlcNAc T-V coding sequences with at least 70%, preferably at least 80%, more preferably at least 90% nucleotide sequence homology to the exemplified rat GlcNAc T-V coding sequence can be identified and isolated from cDNA libraries prepared from mRNA sources other than rat cells, using well-known DNA-DNA hybridization technology and the exemplified rat GlcNAc T-V coding sequence provided herein. Also contemplated are genomic clones encoding GlcNAc T-V, which clones comprise the natural regulatory sequences. It is understood that any intron sequences in genomic GlcNAc T-V are not to be included in sequence comparisions to the exemplified full-length coding sequence.

Additional objects of this invention are DNA molecules containing a first nucleotide sequence encoding an enzymatically active GlcNAc T-V and a second nucleotide sequence not found associated with the GlcNAc T-V coding sequence in nature, termed an exogenous nucleotide sequence herein. Preferably the first nucleotide sequence encodes a polypeptide sequence with GlcNAc T-V activity, said polypeptide having an amino acid sequence as given in FIG. 10 and SEQ ID NO:16.

Still further objects of the invention are cells genetically engineered to contain a DNA molecule containing a first nucleotide sequence encoding an enzymatically active GlcNAc T-V and a second nucleotide sequence not found associated with the GlcNAc T-V coding sequence in nature. Mammalian cells are preferred for recombinant expression of GlcNAc T-V coding sequences. Particularly preferred are COS-7 cells and CHO (Chinese Hamster Ovary) cells. The exemplified rat GlcNAc T-V amino acid sequence is particularly preferred, preferably encoded by the exemplified nucleotide coding sequence as in FIG. 10 or SEQ ID NO:15 from nucleotide 299 through nucleotide 2521.

BRIEF DESCRIPTION OF THE DRAWINGS

FIGS. 5A–5D illustrates autoradiograms resulting from Southern hybridizations using radiolabelled 200 amplimer (PCR product) prepared using rat mammary tumor cell line MAT C1 cDNA from poly(A)+ RNA as template and Primer 1 (SEQ ID NO:5) and Antiprimer 2 (SEQ ID NO:8) as primers. FIG. 5A shows the results for BglII-digestion, FIG. 5B the results for NcoI/XhaI digestion, FIG. 5C for NcoI digestion and FIG. 5D for BamHI/BglII digestion. In each panel, lane 1 contains digested MAT C1 genomic DNA and lane 2 contains digested rat liver genomic DNA.

FIG. 6 is a reproduction of an autoradiogram resulting from a Northern hybridization experiment in which rat kidney mRNA was size-separated by agarose gel electrophoresis and probed with radioactive HindIII/BglI fragment of the mouse partial GlcNAc T-V clone.

FIG. 8 is a reproduction of an autoradiogram resulting from the Southern hybridization of the DNA transferred from the gel illustrated in FIG. 7 in reverse orientation after it was probed with primer A:474-14 (SEQ ID NO: 9).

FIG. 10 sets out the nucleotide sequence analysis (SEQ ID NO:15), including the deduced amino acid sequence (SEQ ID NO:16), of one Rat 1-EJ GlcNAc T-V cDNA clone. Approximately 300 bp of 5' untranslated sequence is revealed, as well as 2220 bp of amino acid coding sequence and approximately 100 bp of the 3' untranslated region. The coding region extends from an ATG starting at nucleotide 299 to a stop codon ending at nucleotide 2521. Each of six possible N-glycosylation sites is marked by an asterisk (*).

FIG. 11 presents the sequences of partial GlcNAc T-V coding sequences, termed amplimer sequences herein, from rat and mouse. Colons (:) indicate identical bases. There appear to be 13 differences between mouse and rat.

DETAILED DESCRIPTION OF THE INVENTION

Figure 1:
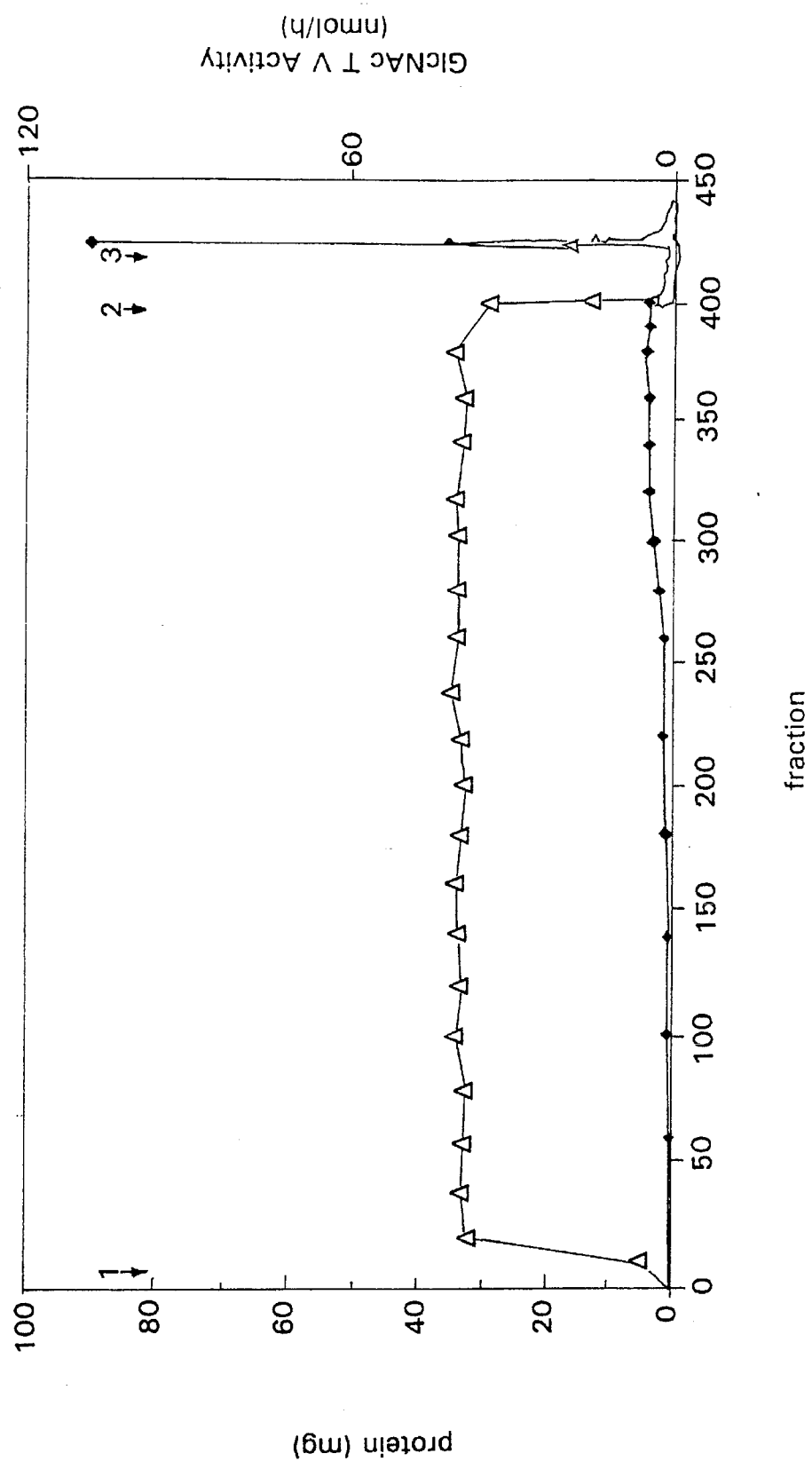
FIG. 1 illustrates the elution profile for rat kidney GlcNAc T-V from UDP-hexanolamine SEPHAROSE. At the first arrow, 3L of freshly prepared and dialyzed Triton extract of acetone powder from rat kidney was applied to a 1.2×7 cm column of UDP-hexanolamine (14 µmol/ml of gel) SEPHAROSE. At the arrow labeled "2," the column was washed with about 400 ml of loading buffer. At the third arrow, the column was eluted with loading buffer, further containing NaCl at a final concentration of 500 mM. Fractions were collected after elution and assayed for protein content (▲) and for GlcNAc T-V activity (♦).
Figure 2:
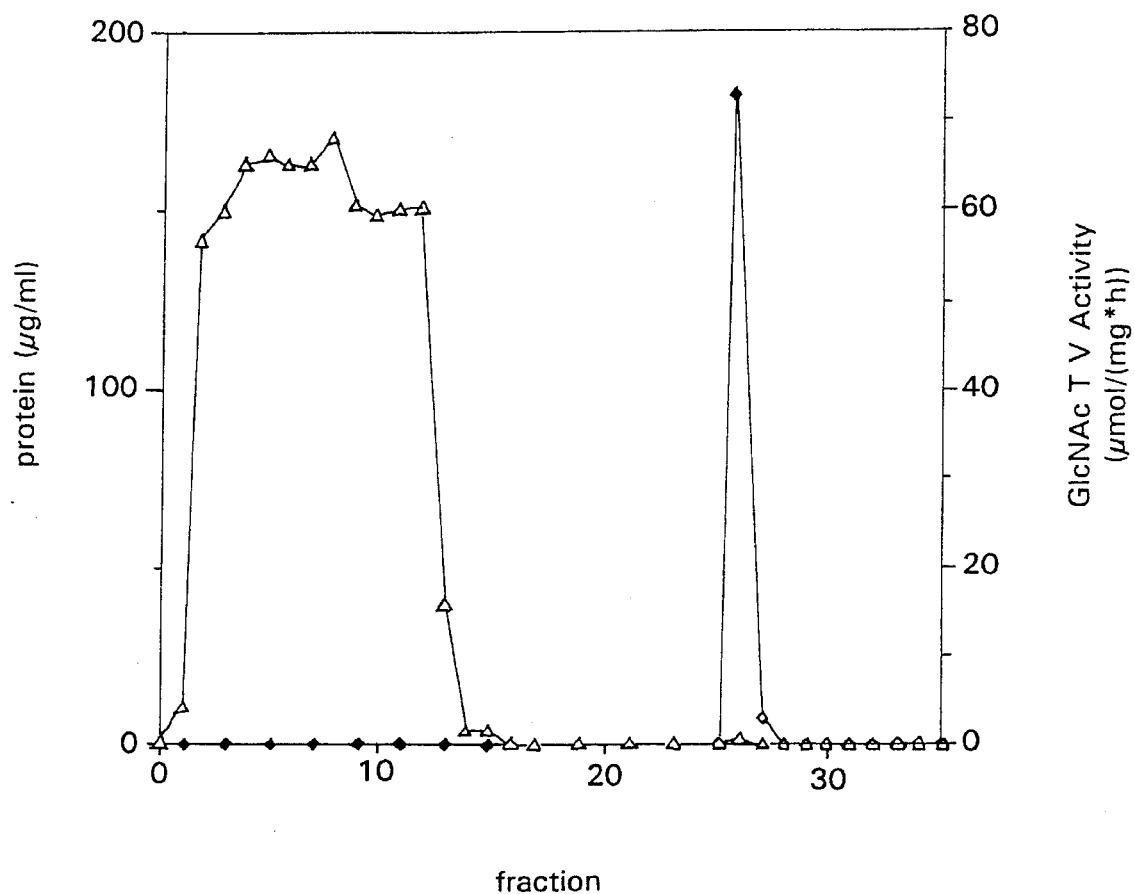
FIG. 2 illustrates the chromatography of rat kidney GlcNAc T-V over an inhibitor-BSA SEPHAROSE column. Pooled and dialyzed fractions from the UDP-hexanolamine column (about 100 ml) were brought to 1 mM UDP-GlcNAc and (at the first arrow) loaded onto a 1.2×3 cm column of inhibitor-BSA-SEPHAROSE pre-equilibrated with loading buffer (50mM sodium cacodylate pH 6.5, 0.1% Triton X-100, 20% glycerol, 0.05% sodium azide). At the second arrow, the column was washed with about 20 ml of loading buffer. At the third arrow, the column was brought to room temperature and eluted with loading buffer which was made 500 mM NaCl and adjusted to a pH of 8.0. Fractions were collected and assayed for protein content (▲) and for GlcNAc T-V activity (♦).

In general, the terminology used herein is standard, as understood by those of ordinary skill in the fields of molecular biology, biochemistry, protein chemistry, and cell biology. For added clarity, certain terms are defined herein. Standard abbreviations are used; these abbreviations are consistent with those used and approved by scientific journals in the field (e.g., Journal of Biological Chemistry, Science, Nature, etc.).

Methods used herein are either specifically referenced or are sufficiently well known as to be available in at least one of several readily accessible published collections of methodologies (See, e.g., Sambrook et al. (1989) *Molecular Cloning, A Laboratory Manual* (2nd ed.), Cold Spring Harbor Laboratory, Cold Spring Harbor, N.Y., Innis et al. (1990) *PCR Protocols: A Guide to Methods and Applications,* Academic Press, New York, N.Y., and references cited therein, all incorporated herein by reference).

Complementary DNA (cDNA) synthesis involves the in vitro synthesis of a double stranded DNA sequence by enzymatic reverse transcription of mRNA isolated from donor cells. In the present invention, polyadenylated RNA is prepared from rat 1-EJ cultured cells (described in Peles et al. (1992) Cell 69:205–216). Rat 1-EJ cells are Rat 1 fibroblasts which have been transfected with the human EJ gene, an activated Harvey ras gene, which is believed to elevate expression levels for GlcNAc T-V. cDNA molecules and/or libraries can be used for isolating a DNA sequence encoding a selected protein when the entire amino acid sequence of that protein is not known. Isolating a gene from a cDNA library is made much easier when at least a partial amino acid sequence is known, and is further facilitated when a complete coding sequence from at least one species is known. Procedures for the preparation of cDNA sequences in plasmid libraries derived from the reverse transcription of mRNA are well-known to the art.

The polymerase chain reaction (PCR) provides a powerful alternative to cDNA cloning for the amplification of sequences encoding a selected protein when at least a partial sequence of the selected protein is known. A degenerate oligonucleotide sequence is prepared according to the complement of the sequence encoding the partial amino acid sequence, and this degenerate oligonucleotide (i.e., a family of sequences) is used to prime PCR synthesis using cDNA derived from polyadenylated RNA as template. Further oligonucleotides for priming PCR are derived from unique (i.e., known) nucleotide sequences.

Expression refers to the transcription and translation of a structural gene (coding sequence) so that a protein having the biological activity of GlcNAc T-V is synthesized.

The term expression control sequence refers to a DNA sequence that controls and regulates the transcription and translation of another DNA sequence (i.e., a coding sequence). A coding sequence is operatively linked to an expression control sequence when the expression control sequence controls and regulates the transcription and translation of that coding sequence. The term "operatively linked" includes having an appropriate start signal (e.g., ATG) in front of the DNA sequence to be expressed and maintaining the correct reading frame to permit expression of the DNA sequence under the control of the expression control sequence and production of the desired product encoded by the DNA sequence. If a gene that one desires to insert into a recombinant DNA molecule does not contain an appropriate start signal, such a start signal can be inserted in front of the gene.

As used herein, an exogenous nucleotide sequence is one which is not in nature covalently linked to a particular nucleotide sequence, e.g., a GlcNAc T-V coding sequence. Examples of exogenous nucleotide sequences include, but are not limited to, plasmid vector sequences, expression control sequences not naturally associated with particular GlcNAc T-V coding sequences, and viral vector sequences.

Similarly, as used herein an exogenous gene is one which does not naturally occur in a particular recombinant host cell but has been introduced in using genetic engineering techniques well known in the art. An exogenous gene as used herein can comprise a GlcNAc T-V coding sequence expressed under the control of an expression control sequence not associated in nature with said coding sequence.

Another feature of this invention is the expression of the sequences encoding GlcNAc T-V. As is well-known in the art, DNA sequences may be expressed by operatively linking them to an expression control sequence in an appropriate expression vector and employing that expression vector to transform an appropriate host cell.

A wide variety of host/expression vector combinations may be employed in expressing the DNA sequences of this invention. Useful expression vectors, for example, may consist of segments of chromosomal, nonchromosomal and synthetic DNA sequences. Suitable vectors include derivatives of SV40 and known bacterial plasmids, e.g., *Escherichia coli* plasmids colE1, pCR1, pBR322, pMB9 and their derivatives, plasmids such as RP4; phage DNAs, e.g., M13 derivatives, the numerous derivatives of phage λ, e.g., λgt11, and other phage DNA; yeast plasmids derived from the 2μ circle; vectors useful in eukaryotic cells, such as insect or mammalian cells; vectors derived from combinations of plasmids and phage DNAs, such as plasmids that have been modified to employ phage DNA or other expression control sequences; baculovirus derivatives; and the like. For mammalian cells there are a number of well-known expression vectors available to the art.

Any of a wide variety of expression control sequences may be used in these vectors to express the DNA sequences of this invention. Such useful expression control sequences include, for example, the early and late promotes of SV40 or adenovirus for expression in mammalian cells, the lac system, the trp system, the TAC or TRC system, the major operator and promoter regions of phage λ, the control regions of fd coat protein, the promoter for 3-phosphoglycerate kinase of phosphatase (e.g., pho5), the promoters of the yeast α-mating factors, and other sequences know to control the expression of genes of prokaryotic or eukaryotic cells or their viruses, and various combinations thereof. The skilled artisan understands which expression control sequences are appropriate to particular vectors and host cells.

A wide variety of unicellular host cells are also useful in expressing the DNA sequences of this invention. These hosts may include well-known eukaryotic and prokaryotic hosts, such as strains of *E. coli*, Pseudomonas, Bacillus, Streptomyces, fungi such as yeasts, and animal cells, such as CHO, R1.1, B-W and L-M cells, African Green Monkey kidney cells (e.g., COS 1, COS-7, BSC1, BSC40, and BMT10), insect cells (e.g., Sf9), and human cells and plant cells in culture.

It is understood that not all combinations of vector, expression control sequence and host cell will function equally well to express the DNA sequences of this invention. However, one skilled in the art will be able to select the proper vector, expression control sequence, and host cell combination without undue experimentation to accomplish the desired expression without departing from the scope of this invention.

In selecting a suitable expression control sequence, a variety of factors will normally be considered. These include, for example, the relative strength of the promoter, its controllability, and its compatibility with the particular DNA sequence or gene to be expressed, e.g., with regard to potential secondary structure. Suitable unicellular hosts will be selected by consideration of factors including compatibility with the chosen vector, secretion characteristics, ability to fold proteins correctly, and fermentation requirements, as well as any toxicity to the host of the product encoded by the DNA sequences to be expressed, and the ease of purification of the expression products. The practitioner will be able to select the appropriate host cells and expression mechanisms for a particular purpose.

Several strategies are available for the isolation and purification of recombinant GlcNAc T-V after expression in a host system. One method involves expressing the proteins in bacterial cells, lysing the cells, and purifying the protein by conventional means. Alternatively, one can engineer the DNA sequences for secretion from cells. See Example 11 and/or Colley et al. (1989) J. Biol. Chem. 264:17619–17622, which reference describes purifying a sialyltransferase by engineering the cleavable signal peptide of human gamma-interferon onto the DNA sequence for the transferase. Larsen et al. (1990) Proc. Natl. Acad. Sci. USA 87:6674–6678, fused the DNA sequence for protein A to the amino-terminal end of a fucosyl transferase gene and expressed it as an excreted fusion protein. In these constructions, one can optionally remove the transmembrane region of these proteins that exists near the amino-terminus. After secretion the proteins are purified from the medium. Similar strategies are available for bacterial expression systems.

N-acetylglucosaminyltransferase V (GlcNAc T-V) denotes the enzyme UDP-N-acetylglucosamine:α-6-D-mannoside β(1,6)-N-acetylglucosaminyltransferase (EC 2.4.1.155). This enzyme is responsible for the synthesis of β-1,6 branch structure (-[GlcNAc-β-(1,6)Man-α(1,6)Man]-) found in both tri-and tetraantennary N-linked oligosaccharides.

It is understood by those skilled in the art that the exemplified rat GlcNAc T-V coding sequence, provided herein in FIG. 10 and in SEQ ID NO:15 from nucleotide 299 through nucleotide 2521, is representative of GlcNAc T-V from other vertebrate sources, especially of other mammalian sources, including humans. The coding sequence for rat GlcNAc T-V provided herein is suitable for use in preparing or deriving PCR primers for identifying and/or amplifying sequences encoding human or other animal GlcNAc T-V, and/or for use as hybridization probes to identify clones encoding human or rat, other mammalian or other vertebrate GlcNAc T-V in appropriate genomic or cDNA libraries.

The techniques for the purification of the rat kidney GlcNAc T-V disclosed herein will be understood to be applicable to the purification of human or other GlcNAc T-V to a level comparable to that of rat kidney GlcNAc T-V. The skilled artisan recognizes that routine modifications of the procedures disclosed herein may provide improved results in isolating nonexemplified GlcNAc T-V enzymes.

Species other than rat, including mouse and human, contain genes encoding proteins which catalyze the same enzymatic reaction as rat GlcNAc T-V, which genes have significant sequence homology to the rat gene encoding GlcNAc T-V. One can isolate these homologous genes using the DNA sequences of this invention as probes or primers under standard hybridization conditions. This invention specifically contemplates and encompasses such sequences.

A comparison of limited nucleotide sequence data (about 160–180 bases) from within the coding sequences of rat, mouse and human, obtained by PCR amplification of mRNA using primers disclosed herein, revealed significant sequence conservation; at least about 90% nucleotide sequence homology was observed in rat-mouse and rat-human comparisons. Thus, GlcNAc T-V coding sequences from vertebrate sources will have significant sequence homology to the exemplified rat GlcNAc T-V coding sequence provided herein. The ordinary skilled artisan can utilize the exemplified sequence or portions thereof preferably at least 25–30 bases in length, in hybridization probes to identify cDNA (or genomic) clones encoding GlcNAc T-V, where there is at least 70% sequence homology to the probe sequence using appropriate art-known hybridization techniques. The skilled artisan understands that the capacity of a cloned cDNA to encode functional GlcNAc T-V enzyme can be readily tested as taught herein (See Example 11).

Hybridization conditions appropriate for detecting various extents of nucleotide sequence homology between probe and target sequences and theoretical and practical consideration are given, for example in B. D. Hames and S. J. Higgins (1985) *Nucleic Acid Hybridization,* IRL Press, Oxford, and in Sambrook et al. (1989) supra. Under particular hybridization conditions the DNA sequences of this invention will hybridize to other DNA sequences having sufficient homology, including homologous sequences from different species. It is understood in the art that the stringency of hybridization conditions is a factor in the degree of homology required for hybridization. The skilled artisan knows how to manipulate the hybridization conditions so that the stringency of hybridization is at the desired level (high, medium, low). If attempts to identify and isolate the GlcNAc T-V gene from another mammalian source fail using high stringency conditions, the skilled artisan will understand how to decrease the stringency of the hybridization conditions so that a sequence with a lower degree of sequence homology will hybridize to the sequence used as a probe. The choice of the length and sequence of the probe is readily understood by the skilled artisan.

When a cDNA library is used as a source of GlcNAc T-V coding sequences, the skilled artisan will take steps to insure that the library is of high quality, i.e., that rare mRNAs will be represented and that large mRNAs (larger than about 3 kb) will be present as full length cDNA clones. If the artisan uses one of the commercially available or otherwise accessible cDNA libraries, he will choose one that meets the criteria taught herein. Providing for rare and/or large message representation is within the skill of the art.

The DNA sequences of this invention refer to DNA sequences prepared or isolated using recombinant DNA techniques. These include cDNA sequences, sequences isolated using PCR, DNA sequences isolated from their native genome, and synthetic DNA sequences. As used herein, this term is not intended to encompass naturally-occurring chromosomes or genomes. Sequences derived from the GlcNAc T-V gene can be used in studying the regulation of GlcNAc T-V expression in normal cells, in transformed cells and in metastatic tumor cells, and can be used in designing mechanisms, e.g., via antisense RNA or DNA, for inhibiting metastasis of tumor cells. These sequences can also be used to direct recombinant synthesis of GlcNAc T-V.

Expression of recombinant DNA molecules according to this invention may involve post-translational modification of a resultant polypeptide by the host cell. For example, in mammalian cells expression might include, among other things, glycosylation, lipidation or phosphorylation of a polypeptide, or proteolytic cleavage of a signal sequence to produce a "mature" protein. Accordingly, as used herein, the term "GlcNAc T-V" encompasses full-length polypeptides and modifications or derivatives thereof, such as glycosylated versions of such polypeptides, mature proteins, polypeptides retaining a signal peptide, truncated polypeptides having comparable biological activity, and the like. Expression of GlcNAc T-V in eukaryotic cell lines expressing biologically active glycoproteins will allow efficient branch structure initiation directed by GlcNAc T-V, where desired.

Rat kidney was the source of the GlcNAc T-V for purification because of the commercial availability of relatively large quantities of the tissue. The purification of rat kidney GlcNAc T-V is described in Shoreibah et al. (1992) supra. A survey of mouse, hamster and rat tissues had revealed that kidney was one of the most abundant sources of the enzyme in these rodents. Purified GlcNAc T-V from rat kidney migrates predominantly as a doublet of 69 and 75 kDa on 10% SDS-polyacrylamide gels.

The first step in the exemplified GlcNAc T-V purification was the preparation of an acetone powder from rat kidney. The acetone powder is thrice extracted with Triton X-100, resulting in the solubilization of over 95% of the activity from the acetone powder. Chromatography over UDP-hexanolamine-SEPHAROSE results in 145-fold purification. Inclusion of EDTA in the column buffer prevents galactosyltransferase and GlcNAc T-I from binding to the support. The substitution of the SEPHAROSE (Pharmacia, Piscataway, N.J.; agarose) at a level of 14 µmoles of UDP-hexanolamine per ml of settled gel is critical; substitution levels of 6 and 9 µmoles per ml gave significantly lower activity yields.

The next step of the purification was chromatography over a synthetic oligosaccharide inhibitor-BSA-affinity column. The ligand in the column is an active site inhibitor which mimics the natural oligosaccharide acceptor of GlcNAc T-V, but contains a hydrogen in place of the reactive 6'-hydroxyl. Chromatography over this resin and elution of bound material with a step gradient of UDP resulted in an additional 2000-fold purification. The purification of rat kidney GlcNAc T-V is summarized in Table 1. The material resulting from these two chromatographic steps resulted in substantially pure enzyme, having a specific activity of approximately 18 µmol/min·mg protein under the assay conditions disclosed herein. This enzyme preparation is stable in the presence of 20% glycerol for several months when stored at 4° C.

TABLE 1

PURIFICATION OF RAT KIDNEY N-ACETYLGLUCOSAMINYLTRANSFERASE V
Results described below are based on a preparation of the enzyme from 300 g of frozen rat kidneys.

| Step | Volume ml | Protein mg | Total Activity nmol/h | Specific Activity nmol/(mg · h) | Yield % | Purification -fold |
|---|---|---|---|---|---|---|
| Rat kidney acetone powder Triton X-100 extract | 3,300 | 13,900 | 2,221 | 0.16 | 100 | 1 |
| UDP-hexanolamine-Sepharose | 96 | 38.0 | 889 | 23.2 | 40 | 145 |
| Inhibitor-BSA-Sepharose | 6 | 0.0078 | 568 | 73,000 | 26 | 450,000 |

To confirm that the two major SDS-PAGE protein bands (69 and 75 kDa) resulting from the two column purification scheme comprised GlcNAc T-V, an aliquot of the purified enzyme preparation was re-chromatographed on a 1 ml UDP-hexanolamineagarose column. The bound material was eluted using several stepwise elutions of the ligand UDP, instead of the single concentration of NaCl, as used in the first chromatographic step. Almost no activity was detected in either the fractions eluted using a UDP concentration of 10 or 20 mM. Fifty mM UDP displaced the majority of the GlcNAc T-V activity from the column. A small peak was eluted using 50 mM UDP plus 150 mM NaCl. As judged by the silver staining pattern, rechromatography did not result in further increases in purity of the GlcNAc T-V. Similar results were obtained when a sample material resulting from the two column purification scheme were re-chromatographed on the inhibitor-BSA affinity column.

Once the GlcNAc T-V was substantially purified, the assay conditions were optimized. Enzymatic activity was stabilized and enhanced by the inclusion of 20% glycerol and 0.5 mg/ml IgG. The optimal pH range for the substantially pure GlcNAc T-V was 6.5 to 7.0; optimal Triton X-100 concentration was in the range of about 1.0 to about 1.5%. Enzyme activity was maximal at about 0.2M NaCl, and was inhibited at higher salt concentrations. Divalent cations had a minimal effect on apparent enzyme activity when added as $MnCl_2$, $CaCl_2$ or $MgCl_2$, and the addition of 20 mM EDTA did not appear to be inhibitory.

Using the optimized assay conditions, kinetic parameters were determined for the substantially pure GlcNAc T-V enzyme. The apparent $K_m$ for the oligosaccharide acceptor ($\beta$GlcNAc(1,2)$\alpha$Man(1,6)$\beta$Man-O-$(CH_2)_8COOCH_3$) was 87 µM, and the apparent $K_m$ for UDP-GlcNAc was 11.0 mM. The apparent $V_{max}$ for the sugar nucleotide was 18.8 µmol/(mg·min).

For amino acid sequence analysis, the enzyme was further purified by preparative SDS-PAGE using an Applied Biosystems High Performance Electrophoresis Apparatus (Applied Biosystems, Foster City, Calif.) which elutes samples from a tube gel and collects fractions. The fractions containing enzyme were pooled and concentrated. The enzyme protein was then precipitated by ethanol addition and lowering the temperature [−20° C.]. The precipitate was collected by centrifugation, washed and dried.

Figure 3:
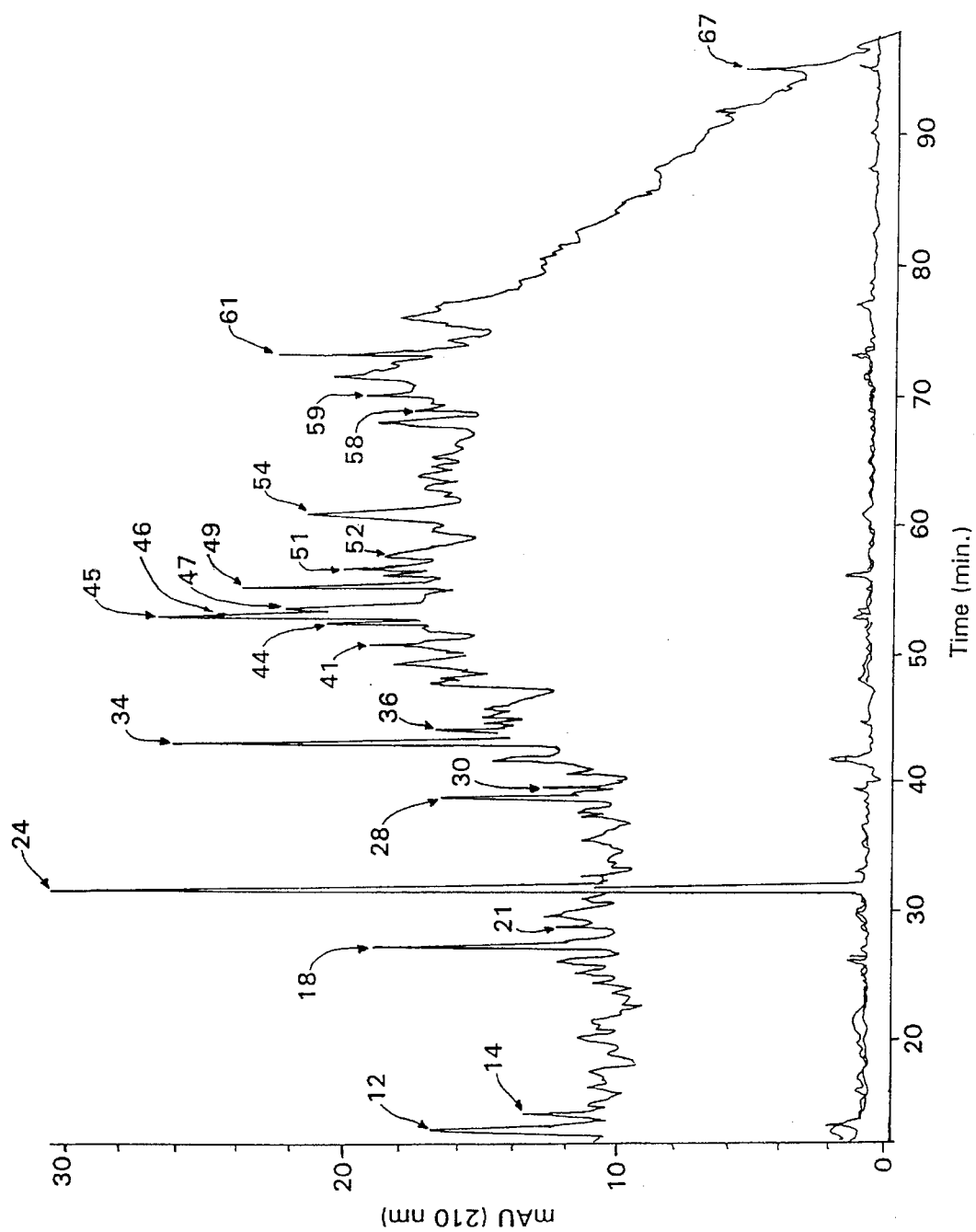
FIG. 3 is a profile of the tryptic peptide digest components resolved by reverse phase HPLC. The vertical axis represents protein content as measured by absorbance at 210 nm and the horizontal axis represents retention time on the column. The peptides of peaks 28, 34, 49 and 61 were selected as candidates for gas phase peptide sequencing.

$NH_2$-terminal amino acid sequencing was attempted, but the results indicated that the N-terminus of the protein was blocked. A sample of the substantially purified GlcNAc T-V from rat kidney was then digested using immobilized trypsin, separated from the immobilized trypsin and the peptides within the digest were then separated by reverse phase HPLC using a 2.1×150 mm VYDAC C18 column, eluted with a gradient of acetonitrile. The elution profile is shown in FIG. 3. Four peaks were chosen for gas phase sequencing (FIG. 3, peaks 29, 34, 49, 61). The results were as follows:

Peak #34 AsnThrAspPhePheIleGlyLysProThrLeuArg (SEQ ID NO:1)
Peak #49 AlaIleLeuAsnGlnLysIleGLuProTyrMetProTyrGluPheThr (SEQ ID NO:2)
Peak #28 ValLeuAspSerPheGlyThrGluProGluPheAsn (SEQ ID NO:3)
Peak #61 SerAspPro[Cys]TyrAla[Asp]Tyr[Glu]Val (SEQ ID NO:4)

Bracketed amino acid residues were assigned with some uncertainty. The amino acid sequences obtained from the four peaks were searched within the Swiss Protein Data Bank and deduced degenerate coding sequences were searched in the Genbank database. No significantly homologous sequences were found.

The determination of a partial amino acid sequence for GlcNAc T-V allows the production of sets of degenerate oligonucleotide probes or primers, thus, enabling the cloning of the corresponding cDNA and genomic clones. Those oligonucleotides can also be used to study the transcriptional and/or translational mechanisms which control the level of expression of the gene encoding GlcNAc T-V.

From the amino acid sequences for the internal peptides corresponding to peaks 34 and 49, corresponding degenerate oligonucleotides were designed for use as primers for PCR amplification of cDNA sequences encoding GlcNAc T-V. The degenerate 29 base oligonucleotide designed from the sequence of first ten amino acids of the Peak 34 peptide is presented as Primer 1 (SEQ ID NO:5). The antisense counterpart (SEQ ID NO:6) of Primer 1, termed antiPrimer 1 herein, will be useful as a primer in the PCR amplification of sequences encoding GlcNAc T-V present within poly-adenylated mRNA populations, prepared from cells including, but not limited to, rat kidney, mouse lymphoma BW5147 cells and ascites-grown rat mammary gland tumor MAT C1 cells.

Primer 1: AAYACIGAYTTYTTYATHGGIAARCCNAC (SEQ ID NO:5)
AntiPrimer 1: GTIGGYTTICCDATRAARAARTCIGTRTT (SEQ ID NO: 6) (antisense)

A second degenerate 29 base oligonucleotide was designed using the sequence of the last ten amino acids of the peptide corresponding to Peak 49:

Primer 2: ATHGARCCITAYATGCCITAYGARTTYAC (SEQ ID NO:7)
AntiPrimer 2: TCRTAIGGCATRTAIGGYTCDATYTTYTG (SEQ ID NO: 8) (antisense)

The antisense primers given above can also be used to amplify mRNA encoding GlcNAc T-V in polymerase chain reactions. Other oligonucleotide primers and "antiprimers" may be designed using the peptide sequences and/or GlcNAc T-V sequences disclosed herein by one of ordinary skill in the art for use in priming PCR synthesis of GlcNAc T-V coding sequences.

The sequences of the antisense primers (AntiPrimers 1 and 2; SEQ ID NO:6 and SEQ ID NO:8) are complementary to those of the corresponding Primers 1 and 2, respectively (SEQ ID NO:5 and SEQ ID NO:7). Either the sense or the antisense primers, or preferably the PCR amplification product of Primer 1 and AntiPrimer 2, can be used as hybridization probes or as PCR primers for screening a rat kidney cDNA library, a rat genomic library or mouse libraries for clones encoding GlcNAc T-V. The primers and antisense primers in appropriate combination can be used to prime PCR reactions using cDNA prepared, for example, from rat kidney cell poly(A)+ RNA. Sequences amplifiable with these primers and antisense primers in PCR reactions will be those encoding portions of GlcNAc T-V.

Figure 4:
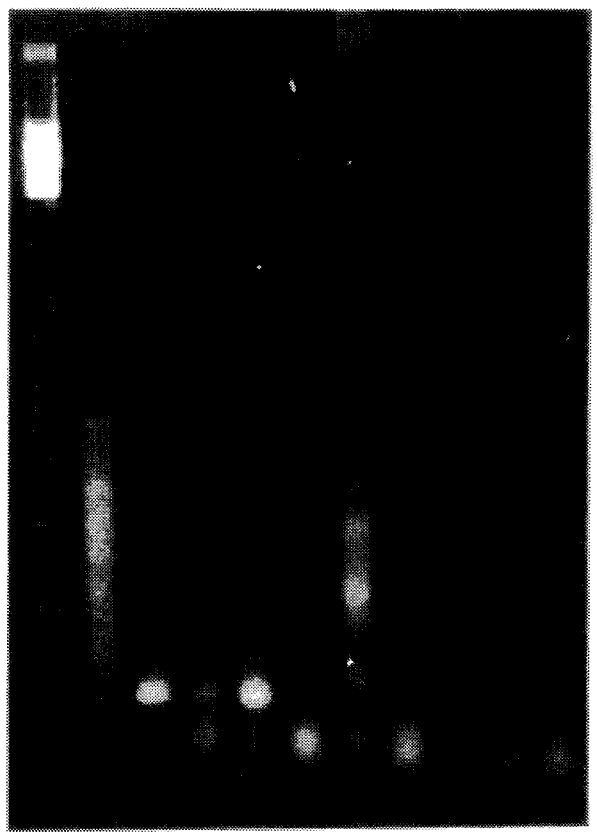
FIG. 4 is a reproduction of an ethidium bromide-stained agarose gel, showing the reaction products of the results of PCR amplification of GlcNAc T-V coding sequences. Lane 1 contains molecular weight standards (123 ladder); Lanes 2 and 7 were the results of reactions containing mouse lymphoma cell line BW5147 cDNA from total RNA as a template; Lanes 3 and 8 were the results of reactions containing mouse lymphoma cell line BW5147 cDNA from poly(A)+ RNA as template; Lanes 4 and 9 were the results of reactions containing rat mammary tumor cell line MAT C1 cDNA from total RNA as template; Lanes 5 and 10 were the results of reactions containing rat mammary tumor cell line MAT C1 cDNA from poly(A)+ RNA as template; and Lanes 6 and 11 were the results for reactions without added template. The reactions run in Lanes 2–6 were carried out with Primer 1 (SEQ ID NO:5) and Antiprimer 2 (SEQ ID NO:8) as the primers for PCR. In the reactions run in Lanes 7–11 were carried out with Primer 2 (SEQ ID NO:7) and Antiprimer 1 (SEQ ID NO:6).

For PCR amplification of sequences encoding GlcNAc T-V, Primer 1 and AntiPrimer 2 cDNA were used to prime PCR-directed DNA synthesis. The combination of Primer 2 (SEQ ID NO:7) and AntiPrimer 1 (SEQ ID NO:6) did not yield an amplification product from either cell line. Using cDNA prepared from poly(A)+ RNA from either the rat mammary tumor line MAT C1 or from the mouse lymphoma cell line BW5147 with Primer 1 and AntiPrimer 2, an amplification product of about 200 bp was obtained, as shown in FIG. 4. These results indicate that the peak 34 sequence (SEQ ID NO:1) is located about 60 amino acids toward the amino end of the protein as compared with the peak 49 amino acid sequence. Background signal was reduced substantially by using 55° C. rather than 50° C. as the annealing temperature in the PCR reactions. The results also indicate a high degree of homology between the GlcNAc T-V coding sequences in mouse and rat. Thus, the primer/antiprimer sequences disclosed herein will be useful in identifying GlcNAc T-V genes and coding sequences of mammals other than rat.

The amplimer made by PCR with cDNA from MAT C1 poly(A)+ RNA as template and Primer 1 (SEQ ID NO:5) and AntiPrimer 2 (SEQ ID NO:8) was $^{32}$P-labelled for use as a hybridization probe. Rat MAT C1 genomic DNA and rat liver genomic DNA were digested in separate restriction endonuclease reactions, the fragments were separated in parallel using agarose gel electrophoresis, blotted to support and DNA-DNA hybridization was carried out under standard hybridization conditions of low stringency. Hybridization patterns were consistent with a single genetic locus encoding GlcNAc T-V in each. FIG. 5 illustrates the autoradiogram obtained for Southern hybridization with rat mammary tumor cell line MAT C1 and for rat liver genomic DNA. With BglII, BamHI/BglII and NcoI digestion, the size of the unique hybridizing genomic band is between 2 and 10 kbp. With NcoI/XhaI digestion, the size of the hybridizing band is between roughly 6 and 9 kb. Routine experimentation will allow size estimation with more precision. The 200 bp amplimer used in this experiment can be used to screen cDNA or genomic libraries to identify GlcNAc T-V sequences. Standard "walking" experiments can be performed to obtain the sequences which flank the hybridizing fragment(s) after cloning of that fragment so that the entire gene can be isolated.

Labelled oligonucleotides having sequences of Primers 1 and 2 (SEQ ID NO: 5 and 7) or AntiPrimers 1 and 2 (SEQ ID NO:6 and SEQ ID NO:8), or preferably the PCR amplification product (amplimer) made using Primer 1 and AntiPrimer 2 as primers, can be successfully used as hybridization probes for screening cDNA libraries prepared from sources including mouse lymphoma BW5147 cells, mouse 3T3 cells and ascites-grown rat mammary gland MAT-C1 cells for sequences encoding GlcNAc T-V.

Figure 6:
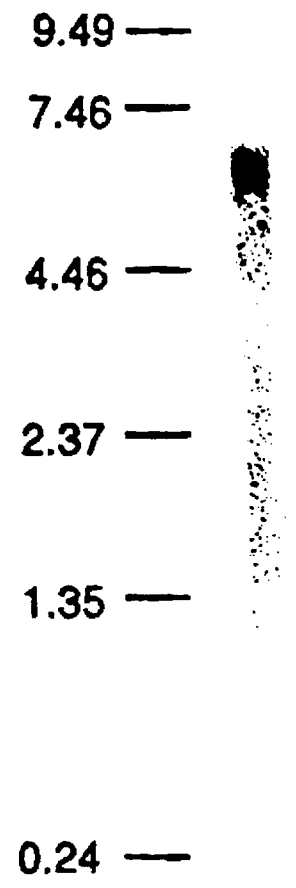

When a restriction fragment from within the coding region of a partial mouse cDNA clone was used as a hybridization probe in a Northern blot of rat kidney mRNA, a band of about 7 kb, along with apparent degradation products, was displayed (See FIG. 6). Thus, the size of the GlcNAc T-V MRNA is large, and care must be taken in preparing (or in choosing) a cDNA library from which to isolate a full length GlcNAc T-V coding sequence.

Examples 7-10 describe the steps in the successful identification and cloning of the rat GlcNAc T-V coding sequence using a PCR-cDNA strategy. In other experiments, an amplimer of about 170–200 bases was prepared by PCR. This amplimer was used to screen a mouse cDNA library, and a partial clone of about 1.7 kb was isolated. Sequence analysis revealed that the long open reading frame did not contain a start codon, and about 300 amino acids were determined by the open reading frame. A series of PCR amplification and screening steps were carried out using plasmid DNA prepared from pools of cDNA clones from subsets of a cDNA library prepared from Rat 1-EJ cell mRNA (See Examples 7-8).

A rat cDNA clone of about 4.8 kb, carrying the full length GlcNAc T-V coding sequence was isolated. A portion of the cDNA was sequenced; that DNA sequence is presented in FIG. 10 and in SEQ ID NO:15. The coding sequence extends from an ATG start codon beginning at nucleotide 299 through a stop codon ending at nucleotide 2521.

The deduced amino acid sequence is given in FIG. 10 and in SEQ ID NO:16. The predicted molecular weight of the encoded GlcNAc T-V, 84,561, is larger than the protein bands observed in and isolated from SDS-PAGE gels. A recent experiment has demonstrated that when GlcNAc T-V is purified from rat kidney in the presence of a cocktail of protease inhibitors in vast excess, a band of about 95 kDa, in addition to the 69 and 75 kDa bands, is observed. When a radioactive photoaffinity active site label was used to tag active enzyme, all three bands were labelled. These observations suggest that the 75 and 69 kDa bands represent proteolytic fragments of the larger protein. The 95 kDa band is likely to represent a glycosylated form of the polypeptide encoded in SEQ ID NO:15. Six potential sites for N-linked glycosylation were identified: Asn residues at amino acid positions 109, 114, 117, 333, 432 and 446 are marked with asterisks in FIG. 10. A putative transmembrane domain, extending from amino acids 14–30, was identified by hydrophobicity analysis using Kyte and Doolittle methodology. This proposed transmembrane domain is characteristic of type II membrane proteins, and is similar to other enzymes of the lumen of the Golgi apparatus.

Within the deduced amino acid sequence of rat GlcNAc T-V (SEQ ID NO:16), the sequences corresponding to the Peak #s 34, 49 and 28 peptide sequences (SEQ ID NOs:1-3) were at amino acids 546–557, 592–607 and 375–386, respectively. The amino acid sequence of Peak #61 (SEQ ID NO:4) occurs at amino acids 168–177 in SEQ ID NO:16. The identities of the cysteine and aspartate residues are confirmed, and the amino acid at the ninth position in SEQ ID NO:4 was deduced to be glycine rather than glutamate, based on the nucleotide sequence in SEQ ID NO:15.

It is well-known in the biological arts that certain amino acid substitutions can be made within a protein without affecting the functioning of that protein. Preferably such substitutions are of amino acids similar in size and/or charge properties. For example, Dayhoff et al. (1978) in *Atlas of Protein Sequence and Structure,* Volume 5, Supplement 3, Chapter 22, pages 345–352, which is incorporated by reference herein, provides frequency tables for amino acid substitutions which can be employed as a measure of amino acid similarity. Dayhoff et al.'s frequency tables are based on comparisons of amino acid sequences for proteins having the same function from a variety of evolutionarily different sources.

Two mouse GlcNAc T-V partial clones have been sequenced. The deduced mouse coding sequence was compared to corresponding rat GlcNAc T-V amino acids 287–740 as in FIG. 10. From the preliminary sequences, the only deduced amino acid difference in the available mouse sequence was at the position corresponding to amino acid 679 of rat. The rat deduced amino acid is isoleucine whereas the mouse amino acid is threonine. A comparison of the available nucleotide sequences over the coding region revealed that there was about 96% sequence homology; a comparison of 103 available bases of rat sequence with mouse sequence in the 3' noncoding region revealed about 88% sequence homology. Thus, the coding and the noncoding sequences (at the 3' end) are highly conserved between mouse and rat, especially within the coding region, where nucleotide differences are in all but one case silent.

The 4.8 kb cDNA insert determined by partial DNA sequence analysis to contain an apparently full length GlcNAc T-V coding sequence was subcloned into the pJT-2 expression vector and electroporated into COS-7 cells (See Example 11). After 3 or 4 days incubation after the electroporation, the transfected cells were harvested, frozen and subsequently assayed for GlcNAc T-V activity. Parallel preparations of cells transfected with pJT-2 without insert DNA served as controls. It was estimated that about 5% of the cells were effectively electroporated. From the data in Table 2, it is clear that the cloned rat cDNA fragment encodes a functional GlcNAc T-V enzyme.

TABLE 2

GlcNAc T-V Activity in the Transient Expression Assay

| Sample | Hrs incubation after electroporation | Specific activity (pmol/mg * hr) |
| --- | --- | --- |
| COS-7 (pJT-2) | 68 | 38 |
|  | 92 | 65 |
| COS-7 (pJT-2-TV) | 68 | 624 |
|  | 92 | 499 |

It will be a matter of routine experimentation for the ordinary skilled artisan to use the DNA sequence information presented herein to optimize GlcNAc T-V expression in a particular expression vector and cell line for a desired purpose. A cell line genetically engineered to contain and express a GlcNAc T-V coding sequence will be useful for the recombinant expression of protein products with the characteristic glycosylation dependent on GlcNAc T-V modification of glycoproteins. Any means known to the art can be used to introduce an expressible GlcNAc T-V coding sequence into a cell to produce a recombinant host cell, i.e., to genetically engineer such a recombinant host cell. Recombinant host cell lines which express high levels of GlcNAc T-V will be useful as sources for the purification of GlcNAc T-V, e.g., for studies of inhibitors of GlcNAc T-V activity for preventing or slowing metastasis of tumors. The coding sequence of GlcNAc T-V will be useful in preparing an antisense construct specific for GlcNAc T-V for inhibiting GlcNAc T-V expression where that is desired, for example, in metastasizing tumor cells.

The following examples are provided for illustrative purposes as well as for enablement. These examples are not intended to limit the scope of the invention. The examples use many techniques well known and accessible to those skilled in the arts of molecular biology and biochemistry. It will be readily apparent to the skilled artisan that modifications of the methods disclosed herein may be made, and that there will be DNA sequence modifications which can be made with the maintenance of the desired result. It will be readily apparent to one of ordinary skill in the art that the nucleotide sequences and amino acid sequences disclosed herein make it unnecessary to repeat many of the examples to practice the invention. All references cited in this application are expressly incorporated by reference herein.

EXAMPLES

EXAMPLE 1

Preparation of UDP-Hexanolamine-Agarose

UDP-hexanolamine was prepared and linked to CNBr-activated SEPHAROSE 4B according to the procedure in Barker et al. (1972) J. Biol. Chem. 247:7135–7147.

EXAMPLE 2

Purification of GlcNAc T-V from Rat Kidney

Frozen rat kidneys were purchased from Pel-Freez Biological, Inc. (Rogers, Ark.).

300 g of frozen rat kidneys were homogenized in 3 liters of cold acetone in a Waring blender at 4° C. All subsequent steps were also performed at 4° C. unless otherwise noted. The acetone-insoluble material was collected on Whatman filter paper no. 4. The acetone insoluble material was re-homogenized in acetone and refiltered. The resulting powder was stirred in 1.8 liters Buffer A (0.1M sodium acetate (pH 6.0), 0.2M NaCl, 0.01M EDTA) for 30 min. The residue was collected by centrifugation for 15 min at 7100×g. The pellet was again extracted with Buffer A and centrifuged again.

The resulting pellet was then stirred in 2 liters water and collected by centrifugation. To the washed residue was then added the following protease inhibitors: 0.1 mM PMSF, 0.05 mg/ml aprotonin, 0.5 mg/ml soybean trypsin inhibitor, 0.5 µg/ml leupeptin, and 1 µg/ml pepstatin. This mixture was then homogenized in 1 liter Buffer B (0.01M Tris-HCl (pH 7.8), 0.4M KCl).

The resulting homogenate was brought to 1% Triton X-100 (w/v) and stirred 30 min. The suspension was centrifuged for 20 min at 7100×g to give the first extract (the supernatant). The pellet was twice again homogenized, solubilized with Triton X-100, and clarified by centrifugation to yield the second and third extracts.

The three extracts were pooled and dialyzed against 20 liters Buffer C (50 mM MES pH 6.5, 0.2% (w/v) Triton X-100, 5 mM EDTA, 0.05% sodium azide over a 72 hr period with a single change of dialysis buffer. The resulting dialysate was clarified by centrifugation and then assayed for protein concentration and enzymatic activity.

In the first affinity chromatography step, 3 l of acetone powder Triton extract was applied to a 1.2×7 cm column of UDP-hexanolamine Sepharose pre-equilibrated with Buffer C. The column was then washed with about 400 ml Buffer C. The column was then eluted with Buffer C plus 0.5M NaCl. Fractions were collected and assayed for GlcNAc T-V activity.

Pooled fractions (about 100 ml) eluted from the UDP-hexanolamine SEPHAROSE column were dialyzed against Buffer C. The dialyzate was brought to 1 mM UDP-GlcNAc and 20% glycerol and was loaded on a 1.2×3 cm column of inhibitor-BSA-Sepharose pre-equilibrated with Buffer D (50 mM MES pH 6.5, 0.1% Triton X-100, 20% glycerol, 0.05% sodium azide. The column was then washed with 20 ml Buffer D without UDP-GlcNAc. Finally the column was stopped, brought to room temperature, and then eluted with the inclusion of 500 mM NaCl in Buffer D in which the pH had been adjusted to 8.0. Fractions were collected and assayed for GlcNAc T-V activity.

An aliquot (0.1 ml) of the pooled active fractions from the inhibitor-BSA affinity column was then dialyzed against Buffer C and applied to a 0.4×8 cm column of UDP-hexanolamine Sepharose pre-equilibrated with Buffer D. The column was then eluted with buffers comprising increasing amounts of UDP in Buffer D: 10 mM UDP, 20 mM UDP, 50 mM UDP, 50 mM UDP with 120 mM NaCl and finally 100 mM UDP with 150 mM NaCl. Fractions were collected and assayed for GlcNAc T-V activity. (For this purification step either Buffer D can be used or 50 mM sodium cacodylate pH 6.5, 0.1% Triton X-100, 20% glycerol, 0.05% sodium azide can be used, with incremental increases in NaCl concentration for elution as described for Buffer D.)

Equal volumes from each set of fractions were concentrated under reduced pressure and elevated temperature with a Speed Vac. SDS-polyacrylamide gel electrophoresis of various fractions was carried out on 10% SDS-polyacrylamide gels after the concentrated samples were boiled in 1×gel sample buffer to reduce and denature the proteins (Laemmli (1970) Nature 227:680–685). The gels were silver-stained as described in Morrisey (1981) Anal. Biochem. 117:307–310 in order to visualize the material.

EXAMPLE 3

Assay of GlcNAc T-V Activity

A typical radiochemical assay for determining activity during purification contained the following reagents which were dried in vacuo in a 1.5 ml conical centrifuge tube: 2 mM ADP (pyrophosphatase inhibitor, 2.5 mM βmethylGlcNAc (β-hexosaminidase inhibitor), $10^6$ cpm UDP-[6-$^3$H]-GlcNAc (10 cpm/pmol) and 1 mM of the synthetic acceptor (β-D-GlcNAc)-(1,2)-α-D-Man-(1,6)-β-D-Man-O-$(CH_2)_8CO_2Me$ in a total volume of 10 microliters.

To initiate the reaction, 0.01 ml of sample, in a buffer containing 50 mM MES pH 6.0, 0.1% Surfact-Amps (Triton) X-100 (Pierce, Rockford, Ill.), was added to the dried reagents and incubated at 37° C. for several hrs.

To terminate the assay, 0.5 ml water was added to each tube, vortexed thoroughly, and the contents of the tubes were centrifuged. The supernatant was then loaded onto a pellicular C18 Sep-Pak column (Millipore, Bedford, Mass.) activated with methanol and pre-equilibrated with water. The columns were washed with 200 ml water to remove water-soluble radioactivity resulting from unreacted substrate and degradation products. The radiolabeled product of the GlcNAc T-V reaction was then eluted with a 0–100% step gradient of methanol, and radioactivity was quantitated by liquid scintillation counting. All assays were conducted in duplicate, and the results were averaged. In tabulating the results for Table I, assays were done in at least two separate experiments and averaged. The variation between the values derived from duplicates or from separate experiments did not exceed ±10% and typically were less than ±2% of the averaged values.

Radiolabeled product was then separated from the unreacted acceptor and radiolabeled UDP-GlcNAc by virtue of the hydrophobic moiety using C-18 chromatography.

Once the GlcNAc T-V protein was purified, the parameters in the assay were optimized: 20% glycerol, near physiological levels of NaCl (about 200 mM), 0.5 mg/ml IgG, pH about 6.5–7.0, and Triton X-100 concentration about 1.0–1.5%.

GlcNAc T-V protein was measured using the enzyme-linked immunosorbent assay described in Crawely et al. (1990) Analytical Biochem 185:112–117. The ELISA uses unlabeled UDP-GlcNAc and a trisaccharide acceptor (β-D-GlcNAc)-(1,2)-α-D-Man-(1,6)-β-O-Man-D-$(CH_2)_8CO_2Me$ coupled to BSA. This assay relied on the use of a polyclonal antibody specific for the tetrasaccharide-BSA product of the GlcNAc T-V reaction. Due to the extreme sensitivity of the ELISA, column fractions column fractions containing an inhibitory amount of NaCl, for example, could be assay without prior dialysis by simply diluting the samples. Standard calibration curves were generated in each assay and absorbance (or relative activity) was correlated to a specific activity by comparison to values obtained for a sample of known GlcNAc activity, as measured in the radiochemical assay.

EXAMPLE 4

Measurement of Small Amounts of Protein

The BCA protein assay (Pierce, Rockford, Ill.) was adapted for use in a microtiter plate format using standard polystyrene 96 well plates (Pierce, Rockford, Ill.) to assay column fractions for protein content during purifications. BSA served as the standard protein.

EXAMPLE 5

Preparation of Inhibitors, Acceptors, Substrates and Affinity Adsorbents

UDP hexanolamine was synthesized and linked to CNBr-activated agarose support (SEPHAROSE 4B) as described in Barker et al. (1972) J. Biol. Chem. 247:7135–7147. The concentration of the ligand relative to the support was 14 μmoles per ml of settled gel.

The deoxy oligosaccharide inhibitor of GlcNAc T-V activity (n-octyl 6-O-[2-O-(2-acetamido-2-deoxy-β-D-glucopyranosyl)-6-deoxy-α-D-mannopyranosyl]-β-D-glucopyranoside) was synthesized as described in Palcic et al. (1990) J. Biol. Chem. 265:6759–6769, and used in assays.

A similar GlcNAc T-V oligosaccharide inhibitor (βGlcNAc(1,2) 6-deoxy-α-Man(1,6) βMan-O-$(CH_2)_8COOCH_3$ was coupled to BSA according to the method of Pinto et al. (1983) Carbohydr. Res. 124:313–318 for use as an affinity chromatography ligand. The inhibitor oligosaccharide (4.1 mg) was converted to the acyl azide as a 25 mM solution in DMF (dimethyl formamide) at −15° C. and then 222.2 mg BSA (Sigma Chemical Co., St. Louis, Mo.) was added in 2 ml of 0.35M $KHCO_3$ and 0.07M $Na_2B_4O_7$ (pH 9.0). The resulting solution was held at 4 C. for 24 h, and then extensively dialyzed against distilled water on a Amicon PM-10 ultrafiltration membrane (Amicon, Inc., Division of WR Grace, Danvers, Mass.). The dialysate was then lyophilized, and redissolved. Protein content was measured using the Bradford assay (Bradford (1976) Analyt. Biochem. 72:248–254) with BSA as a standard. Carbohydrate content was measured using the phenol-sulfuric acid method (Dubois et al. (1956) Analyt. Chem. 28:350– 256. The results indicated that 13 oligosaccharide molecules were incorporated per molecule of BSA (67% coupling).

The coupling of 3.6 mg of the inhibitor-protein complex to 3 ml of periodate-oxidized agarose (SEPHADEX CL-6B, Pharmacia, Piscataway, N.J.) was carried out as described in Stults et al. (1989) Analyt. Biochem. 180:114–119 with $NH_2(CH)_2OH$—HCl as the final blocking reagent. A coupling of 34% of the oligosaccharide-BSA complex to the agarose gave a final incorporation of 0.07 μmol of ligand oligosaccharide per ml of settled gel as estimated by the Bradford protein assay.

Trisaccharide oligosaccharide acceptors and their syntheses are described in Palcic et al. (1990) supra; Pierce et al. (1987) Biochem. Biophys. Res. Commun. 146:679–684; Arango et al. (1988) J. Cell. Biochem. 37:225–231; and Srivastava et al. (1988) Carbohydr. Res. 179:137–161.

EXAMPLE 6

Production of Antibodies Specific for GlcNAc T-V

GlcNAc T-V is precipitated from storage buffer by adding 3 volumes of absolute ethanol and left to stand for 30 min at 4° C. The precipitated protein is collected by centrifugation (10,000×G for 10 min), resuspended in 0.3 ml of Buffer D, and mixed with 1.0 ml of Freund's complete adjuvant. The resulting emulsion is administered to two rabbits by injecting intradermally in the back with 50–75 μl/site or about 75 μg protein per site. Each rabbit receives booster injections of 150 μg per dose, prepared in the same way, 14 days after the initial dose, and each rabbit receives 75 μg at 21, 34, 57 and 64 days after the initial injection. 10–20 ml of blood is collected from an ear vein of each rabbit at weekly intervals, and serum is prepared and stored at −20° C. Relative levels of antibody specific for GlcNAc T-V are estimated by determining the amount of serum required to inhibit 50% of the activity in the assay using the artificial substrate as acceptor. Serum samples with the highest activity are pooled.

Monoclonal antibodies specific for rat kidney GlcNAc T-V are prepared according to standard procedures (e.g., Campbell (1984) *Monoclonal Antibody Technology: Laboratory Techniques in Biochemistry and Molecular Biology* (Burdon and van Knippenberg, eds.) Vol. 13, Elsevier, Amsterdam; Harlow and Lane (1988) *Antibodies: A Laboratory Manual*, Cold Spring Harbor Laboratory, Cold Spring Harbor, N.Y.) after immunization of mice with purified rat kidney GlcNAc T-V.

EXAMPLE 7

Isolation of PCR Fragment Containing Rat GlcNAc T-V Sequences

A. Rat 1-EJ cDNA Library Construction

The Rat 1-EJ cDNA library had been previously constructed. Messenger RNA was isolated by standard procedures (Maniatis et al., 1982) from Rat 1 cells which had been transfected with the human EJ gene, an activated Harvey ras gene (Peles et al. (1992) Cell 69:205–216). Poly (A)$^+$ mRNA was selected using an mRNA separator kit (Clontech Lab, Inc., Palo Alto, Calif.) and cDNA was synthesized with the Superscript kit (BRL Life Technologies, Inc., Bethesda, Md.). Column-fractionated double-stranded cDNA was ligated into SalI and NotI-digested pSPORT-1 plasmid vector (BRL Life Technologies, Inc., Bethesda, Md.) and transformed into *Escherichia coli* DH10B cells by electroporation (Dower et al. (1988) Nucl. Acids Res. 16:6127–6145) The SalI site is on the 5' side and the NotI site is on the 3' side of the cDNA sequence of each clone. Transformed *E. coli* DH10B cells were propagated as 43 individual pools and plasmid DNA was isolated from each pool.

B. Design and Construction of Oligonucleotides

The approximately 200 bp PCR amplimer sequences from mouse, rat and human were analyzed, and specific oligonucleotides were designed covering areas where the mouse, rat and human sequences were identical.
Primer A: 474-14 GGGCCGATGAAGACTTCTGCG (SEQ ID NO: 9) (antisense)
Primer B: 474-16 GGGCTACTTCCTCTCGGTTATTGAG (SEQ ID NO: 10) (antisense)

In addition, an oligonucleotide was designed using the T7 promoter sequence of the cloning vector pSPORT-1.
Primer T7: 476-30 GCTCTAATACGACTCACTATAGG (SEQ ID NO: 11) (sense)

C. PCR Amplification of Rat 1-EJ cDNA Library Sequences

An aliquot of plasmid DNA from each pool of the Rat 1-EJ cDNA library was combined to form a Rat 1-EJ cDNA library DNA mixture (Rat 1-EJ cDNA pool). PCR was carried out on the Rat 1-EJ cDNA pool using primers T7:476-30 (SEQ ID NO: 11) and B:474-16 (SEQ ID NO: 10). The T7 sequence of pSPORT-1 lies upstream from the 5' SalI cloning site used in the cDNA synthesis. Therefore, PCR priming using the oligonucleotide T7:476-30 (SEQ ID NO: 11) synthesizes an amplimer covering the extreme 5' end of the cDNA and extending in the direction of the 3' end of the coding sequence. The PCR product extends into the coding sequence to the primer B:474-16 (SEQ ID NO: 10) which lies within the approximately 200 bp amplimer.

PCR was carried out using a GeneAmp DNA Amplification Kit (Perkin Elmer Cetus, Norwalk, Conn.) according to the manufacturer's instructions. Briefly, a 100 μl reaction consisted of the following:

| |
|---|
| 8 μl MgCl$_2$ 25 mM |
| 10 μl 10X PCR buffer |
| 70.8 μl sterile H$_2$O |
| 2 μl dGTP 10 mM |
| 2 μl dATP 10 mM |
| 2 μl dTTP 10 mM |
| 2 μl dCTP 10 mM |
| 1 μl T7: 476–30 primer 15 μM |
| 1 μl B: 474–16 primer 15 μM |
| 500 ng Rat 1-EJ cDNA library pool DNA |

The reaction mix was overlayered with mineral oil (Sigma, St. Louis, Mo.) and placed in a DNA thermal cycler (Perkin Elmer Cetus). Taq polymerase (0.5 μl, 2.5 U) was added in a hot start procedure and the thermal cycler was programmed as follows:

| | | |
|---|---|---|
| 1 min | 94° C. | |
| 1 min | 59° C. | |
| 2 min | 72° C. | 40 cycles |
| 10 min | 72° C. | |
| soak | 4° C. | |

Figure 7:
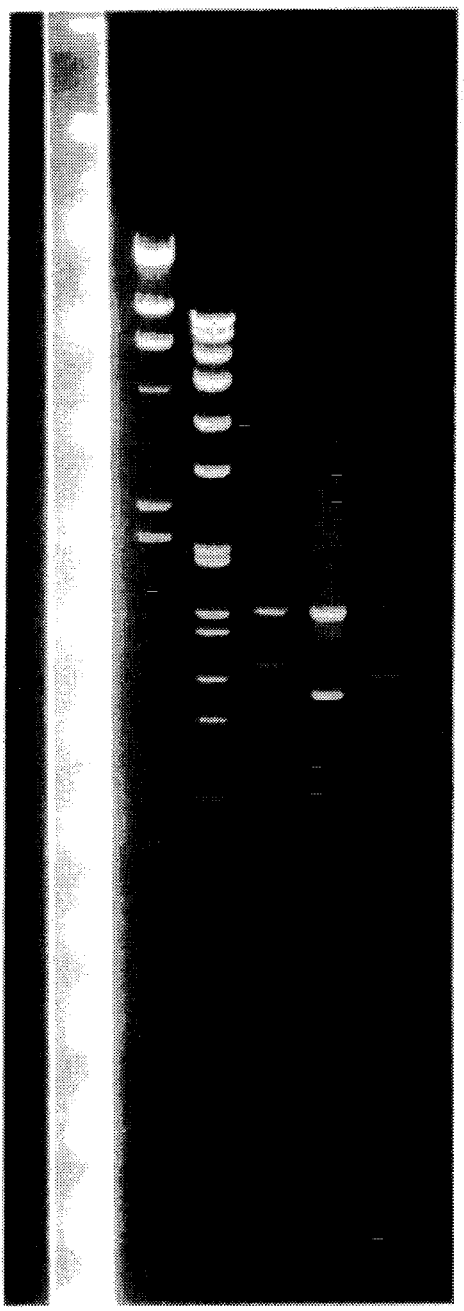
FIG. 7 is a reproduction of an ethidium bromide-stained agarose gel, showing the products obtained after PCR amplification of Rat 1-EJ library cDNA sequences. Lane 1 contains molecular weight standards (Molecular Weight Marker II, Boehringer Mannheim, Indianapolis, Ind.); Lane 2 contains molecular weight standards (Molecular Weight Marker VII, Boehringer Mannheim); Lane 3 contains an aliquot of PCR reaction products resulting from amplification of Rat 1-EJ cDNA using primer T7:476-30 (SEQ ID NO: 11) and primer B:474-16 (SEQ ID NO: 10).
Figure 7:
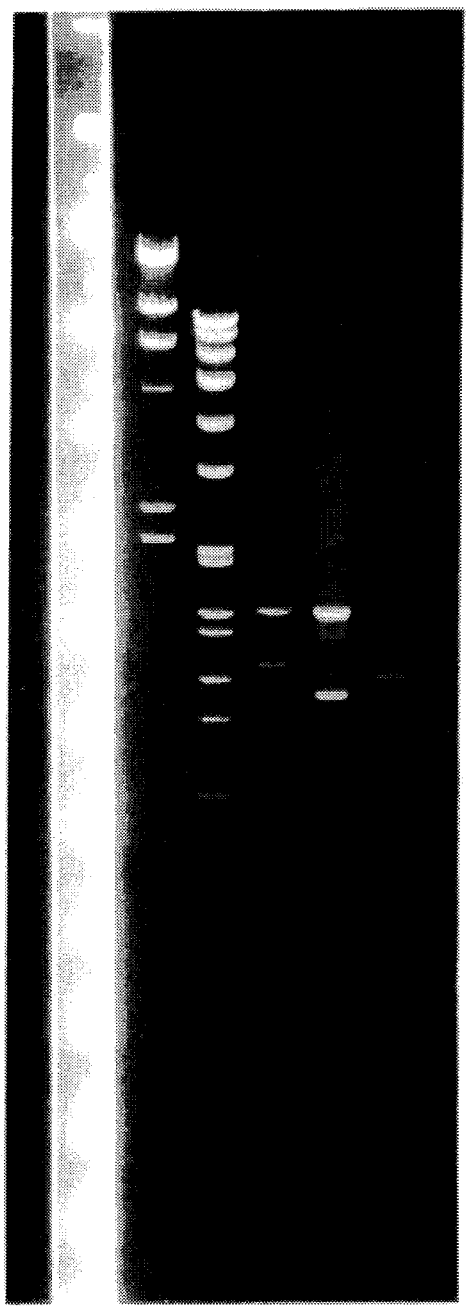

An aliquot of the reaction products was analyzed by agarose gel electrophoresis (0.8% agarose in Tris Borate EDTA buffer (TBE) containing ethidium bromide) and the gel was photographed (FIG. 7). One major band at approximately 1200 bp and several smaller minor species were visible on the ethidium bromide-stained gel.

D. Southern Hybridization of PCR Products

After PCR, products from Example 7, Part C, were separated by agarose gel electrophoresis and analyzed by a standard Southern blot procedure. Briefly, the gel was denatured by soaking in 1.5M NaCl, 0.5N NaOH for 30 min. The gel was then neutralized by soaking in 1.5M NaCl, 0.5M Tris-HCL (pH 7.5) for 30 minutes. The DNA in the gel was transferred to nitrocellulose by capillary action in 10×SSC overnight. After transfer, the nitrocellulose was rinsed in 6×SSC, air dried and crosslinked in a UV Stratalinker (Stratagene, La Jolla, Calif.).

The nitrocellulose was prehybridized, hybridized and probed using an Enhanced Chemiluminescence 3' Oligolabelling and Detection System kit (Amersham, Arlington Heights, Ill.) according to the manufacturer's instructions. Prehybridization was carried out at 50° C. for 30 min. Hybridization was carried out for about one and a half hours at 50° C. with approximately 8 ng/ml of oligonucleotide probe A: 474-14 (SEQ ID NO: 9).

After hybridization, the nitrocellulose was washed twice in 5×SSC, 0.1% SDS at room temperature for 5 min each time. Then the nitrocellulose was washed twice in 1×SSC, 0.1% SDS at 50° C. for 15 min each time. Horse Radish Peroxidase Antibody development and ECL detection were carried out according to kit instructions.

The nitrocellulose was exposed to x-ray film at room temperature for 20 minutes. Autoradiography of the nitrocellulose revealed a single band of approximately 2.1 kb (FIG. 8). This specific, but rare, PCR product was not visible on the ethidium bromide-stained gel (FIG. 7).

E. Amplification of Specific PCR Product

Since the specific 2.1 kb PCR product described in Example 7, Part D was present in such minute quantities that it could only be detected by autoradiography, it was amplified by PCR. First, the 2.1 kb PCR product was isolated by cutting a region of an agarose gel in which the specific DNA was expected to have migrated. The DNA was eluted from the gel using an S&S Elu-Quik DNA Purification Kit (Schleicher & Schuell, Keene, N.H.) following the manufacturer's directions. A PCR reaction was carried out on an aliquot of the eluted DNA utilizing primer T7: 476-30 (SEQ ID NO: 11) at the 5' end. The 3' primer was as follows:
485-26 GGGTACGTGTGAATGATATCCAGGTAG (SEQ ID NO: 12) (antisense)

This oligonucleotide sequence lies approximately 350 bp upstream from the 3' end of the 2.1 kb PCR fragment. This sequence was elucidated by sequencing a partial mouse cDNA which was isolated by screening a mouse lymphoma BW 5147 library with the approximately 200 bp PCR amplimer sequence.

A 100 μl PCR reaction using the eluted 2.1 kb PCR fragment as template was prepared as follows:

```
    8 μl MgCl₂ 25 mM
   10 μl 10X PCR buffer
 61.5 μl sterile H₂O
    2 μl dGTP 10 mM
    2 μl dATP 10 mM
    2 μl dTTP 10 mM
    2 μl dCTP 10 mM
    1 μl T7: 476–30 primer 15 μM
    1 μl 485–26 primer 15 μM
   10 μl eluted 2.1 kb PCR fragment
```

The reaction mix was treated as described in Example 7, Part C and the thermal cycler was programmed as follows:

```
94° C.  30 sec  ⎫
60° C.   1 min  ⎬ 40 cycles
72° C.   1 min  ⎭
72° C.  10 min
 4° C.  soak
```

Figure 9:
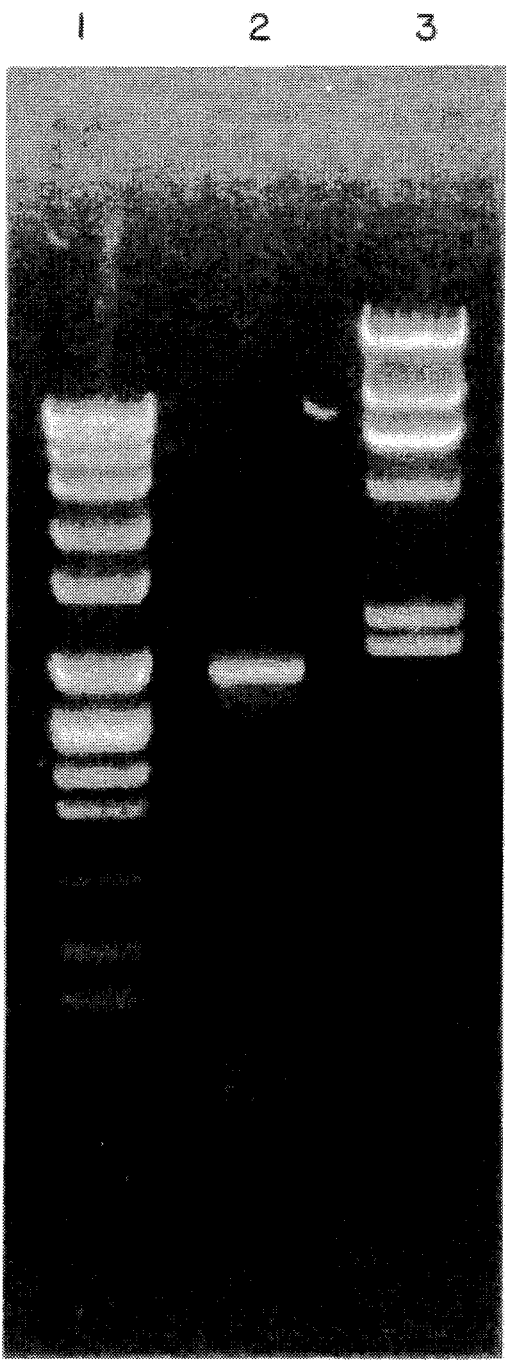
FIG. 9 is a reproduction of an ethidium bromide-stained agarose gel, showing the products obtained after PCR amplification of an approximately 2.1 kb PCR product that was visualized in the autoradiogram in FIG. 8. Lane 1 contains molecular weight standards (Molecular Weight Marker VII, Boehringer Mannheim); Lane 2 contains the PCR products obtained after amplification of the approximately 2.1 kb PCR fragment with primer T7:476-30 (SEQ ID NO: 11) and primer 485-26: (SEQ ID NO: 12); Lane 3 contains molecular weight standards (Molecular Weight Marker II, Boehringer Mannheim).

An aliquot of the reaction products was analyzed by agarose gel electrophoresis (0.8% agarose in TBE containing ethidium bromide) and the gel was photographed (FIG. 9). Analysis of the ethidium bromide-stained gel revealed a single DNA band of approximately 1.8 kb.

F. DNA Sequence Analysis

The approximately 1.8 kb PCR product described in Example 7, Part E was sequenced using Taq DyeDioxy Terminator cycle sequencing kits (Applied Biosystems, Inc., Foster City, Calif.) and an automated DNA sequencer (Applied Biosystems 373A) following the manufacturer's instructions. The PCR fragment was sequenced after it was passed over a Centricon-100 unit (Amicon, Beverly, Mass.) and washed with sterile water. In some instances, sequences were derived after the PCR fragment was subcloned into a pUC13 vector (Promega, Madison, Wis.). Nucleotide sequencing was carried out using synthetic oligonucleotides as primers.

Sequencing of approximately 1750 bp of the PCR fragment and analysis of all possible reading frames revealed overlap with the partial mouse BW 5147 cDNA sequence. The partial mouse cDNA contained 3' untranslated sequence as well as an open reading frame of approximately 885 bases which would code for approximately 295 amino acids, but no start codon. The sequencing of the PCR fragment extended the open reading frame coding region by an additional approximately 445 amino acid residues and located the methionine specifying ATG start codon. In addition, approximately 300 bp of 5' untranslated region was identified in the PCR fragment.

Alternatively, cDNA clones encoding GlcNAc T-V can be isolated using the following strategy.

Total RNA is prepared in parallel isolations from rat kidney tissue, according to standard procedures, and from mouse lymphoma BW5147 cells and from ascites-grown rat mammary gland MAT-C1 cells, as described in Sambrook et al. (eds.) (1989) supra. ATCC T1B47 is a clone (BW5147.3) of the BW5147 cell line adapted into culture (J. Natl. Cancer Inst. (1973) 51:883; J. Immunol. (1973) 110:1470). MAT C1 cells are described in Carraway et al. (1976) J. Biol. Chem. 251:6173–6178. The Poly(A)+ fraction of the total RNA is prepared by chromatography over Oligo(dT) cellulose chromatography as described in Sambrook et al. (eds.) (1989) supra. Polyadenylated mRNA encoding GlcNAc T-V is included within the Poly(A)+ RNA thus prepared.

cDNA libraries are prepared using the poly(A)+ RNA prepared from rat kidney, mouse lymphoma BW5147 cells, and MAT-B1 cell total RNA according to the procedure of Sambrook et al. (eds.) (1989) supra. Cloning of the cDNA population into a suitable vector (such as λgt11) is done according to standard protocols. (See, e.g., Huynh et al. (1985) in *DNA Cloning, a Practical Approach*, Vol. 1 (Glover, D. M., ed.), IRL Press, Washington, D.C., pp. 49–78.)

Commercially-available cDNA libraries (e.g., rat kidney cDNA library, Clontech Laboratories, Palo Alto, Calif.) can also be screened for GlcNAc T-V clones.

The cDNA libraries are screened for sequences encoding GlcNAc T-V by plaque hybridization under low stringency conditions using the approximately 200 bp amplimer radiolabelled by random hexamer labelling as described in Sambrook et al. (eds.) (1989) supra. Clones specifically hybridizing the amplimer sequence are selected for further analysis (restriction endonuclease digestion, nucleotide sequence determination).

Genomic clones encoding GlcNAc T-V can be identified from a rat (or mouse or other mammal) genomic library using Primer 1 (SEQ ID NO:5) or Primer 2 (SEQ ID NO:7) e.g., or Primers 1 and 2 in combination, or the amplimer where PCR synthesized as above was primed with Primer 1

(SEQ ID NO: 5) and AntiPrimer 2 (SEQ ID NO:8) to identify appropriate genomic sequences.

From the clones analyzed it is possible to reconstruct the entire coding sequence of GlcNAc T-V. If a full-length coding sequence is not reconstructed, further primers can be designed using sequences near the ends of the sequenced region for use in the RACE procedure (Rapid Amplification of cDNA Ends) as described in Frohman et al (1988) Proc. Natl. Acad. Sci. USA 85:8998–9002. Where the entire gene is desired, genomic libraries can be screened, and "walking" procedures known in the art are used to extend in both directions.

EXAMPLE 8

Cloning of a Rat cDNA Sequence Encoding GlcNAc T-V

A. Southern Hybridization of Rat 1-EJ Library Pools

Nitrocellulose filters, containing NotI-linearized plasmid DNA from each of the individual 43 pools of the Rat 1-EJ cDNA library, were probed in order to identify which pool(s) contained a full-length GlcNAc T-V cDNA. A cDNA probe was derived from the partial mouse cDNA coding region and was obtained as a HindIII/PstI fragment starting approximately 855 bp down stream from the Rat 1-EJ PCR fragment ATG sequence and extending approximately 650 bp toward the 3' end of the sequence.

The nitrocellulose filters were incubated with prehybridization solution at 42° C. as described in Sambrook et al., (eds.) (1989) supra. Hybridization was then carried out in an overnight incubation using an approximately 650 bp mouse cDNA probe which was labeled with [$\alpha^{32}$P]-dCTP using a Multiprime DNA Labelling System kit (Amersham). The nitrocellulose was then washed and the filters were exposed to X-ray film with an intensifying screen at −80° C. overnight. Autoradiography of the filters revealed 4 positive pools among the 43 screened.

B. PCR Analysis of Rat 1-EJ Library Pools

PCR was carried out using template DNA from each of the 4 positive Rat 1-EJ cDNA library pools identified in Example 8, Part A in order to determine which pool contained a full-length cDNA. The reactions were carried out as described in Example 7, Part C, except that the following primers were used:
Primer 501-16 CCCGTCGACGAGAGCCAAGGGAATG-GTAC (SEQ ID NO: 13) (sense)
Primer 496-2 CCCAGCAGGTACAGAGATGTG (SEQ ID NO: 14) (antisense )

Primer 501-16 (SEQ ID NO: 13) was determined by sequencing the Rat 1-EJ PCR fragment to hybridize in the 5' untranslated region approximately 15 to 35 bases upstream from the ATG start codon. Primer 496-2 (SEQ ID NO: 14) was determined by sequencing to hybridize within the coding region about 900 bases downstream from the ATG start coon. Therefore, PCR with these two primers gives a predicted product of about 900 bp in length covering the 5' end of the coding region. The thermal cycle was programmed as follows:

| 94° C. | 30 sec | |
| 55° C. | 1 min | ] 40 cycles |
| 72° C. | 1 min | |
| 72° C. | 10 min | |
| 4° C. | soak | |

An aliquot of the reaction mixture was separated by agarose gel electrophoresis as described in Example 7, Part C. Analysis of the ethidium bromide-stained gel indicated two of the four pools gave the correct size band (about 900 bp). This information, together with the size of the bands obtained by Southern hybridization of the Rat 1-EJ cDNA library pools (Example 8, Part A) revealed that one pool could contain a full-length GlcNAc T-V cDNA.

C. Colony Hybridization Procedures for Screening a Rat 1-EJ cDNA Library Pool

Transformed E. coli from the glycerol stock of the one pool of the Rat 1-EJ cDNA library identified in Example 8, Part B, above, were spread out at a density of approximately 4,500 colonies per 10×10 cm plate on nutrient plates containing 50 μg/ml Ampicillin. Nitrocellulose filters were used to lift the colonies off the plate. The filters (colony side up) were treated by serially placing them over a piece of Whatman 3 MM paper saturated with each of the following:

1. 1.5M NaCl, 0.5N NaOH for 10 min
2. 1.5M NaCl, 0.5M Tris-HCl (pH 7.5) for 5 min
3. 2×SSC for 5 min The filters were then air dried and crosslinked by UV irradiation. The filters were then subjected to digestion with Proteinase K by incubating in a solution containing 0.2% SDS, 100 mM Tris-HCl (pH 8.5), 50 mM NaCl, 10 mM EDTA (pH 8) and 50 μg/ml proteinase K at 55° C. for 30 min. The filters were then transferred to a solution containing 5×SSC, 0.5% SDS and 1 mM EDTA (pH 8) and incubated at 55° C. for 30 min. Prehybridization, hybridization and subsequent treatments were carried out using an ECL 3' Oligolabelling and Detection System kit (Amersham) with the following conditions:

1. prehybridization was carried out at 53° C. for approximately 2 hours.
2. hybridization was carried out at 53° C. in an overnight incubation using primer 501-16 (SEQ ID NO: 13) at approximately 7 ng/ml.

After hybridization, the filters were washed as described in Example 7, Part D. After ECL detection, the filters were exposed to X-ray film at room temperature for 4 minutes.

Among the 36,000 colonies screened, 24 individual colonies and mixtures of colonies were picked for further analysis by PCR. PCR was carried out in the same manner as described in Example 8, Part B except that a 20 μl reaction volume was used and the template was obtained by touching a pipet tip to the bacterial plate and then dipping the pipet tip in the PCR mixture. After overlayering with mineral oil, the PCR tubes were incubated in the thermal cycler at 94° C. for 4 min prior to adding 0.2 μl of Taq polymerase. The following temperature regime was applied:

| 94° C. | 30 sec | |
| 53° C. | 1 min | ] 25 cycles |
| 72° C. | 1 min | |
| 72° C. | 10 min | |
| 4° C. | soak | |

An aliquot of the reaction mixture was separated by agarose gel electrophoresis as described in Example 7, Part C. Analysis of the ethidium bromide-stained gel revealed three positives among the 24 mixtures examined.

The 3 positive mixtures were replated and probed with primer 496-2 (SEQ ID NO: 14) as described above. Prehybridization and hybridization, according to instructions in the ECL 3' Labelling and Detection System kit, were carried out at 53° C. for 30 min and approximately 2 hours respectively. Washes were as described above and autoradiography was carried out for 20 min at room temperature. Analysis of the X-ray film revealed one positive among approximately 600 colonies screened. This colony was confirmed by PCR analysis with primers 501-16 (SEQ ID NO: 13) and 496-2 (SEQ ID NO: 14) as described above except the reaction volumes were 50 μl.

The one positive colony mixture from above was replated at low density and probed with primer 496-2 (SEQ ID NO: 14) as described above except prehybridization and hybridization were carried out at 55° C. Filters were exposed to X-ray film for 2 min revealing 7 positives among approximately 300 colonies screened.

D. Sequencing Analysis of Rat 1-EJ cDNA

Plasmid DNA was isolated from 4 of the final positive colonies described in Example 8, Part C. Restriction enzyme analysis revealed that the plasmids each contained an approximately 4.8 kb cDNA insert. Nucleotide sequence analysis of one of the plasmids was carried out using the procedures described in Example 7, Part F. Results obtained to date are shown in FIG. 10.

In FIG. 10, the initial DNA sequence designates the sense strand of approximately 300 bases in what appears to comprise the 5' untranslated region preceding the translated portion of the rat GlcNAc T-V cDNA. The sequence immediately following is seen to code for the amino acid sequence of rat GlcNAc T-V. This region spans 2220 bases and codes for 740 amino acids and a stop codon (TAG). The subsequent sequence appears to be an untranslated 3' region of the rat GlcNAc T-V cDNA. By restriction mapping analysis of the plasmid DNA, this 3' untranslated region of the cDNA appears to be approximately 2300 bases in length. Only the first approximately 100 bases of the 3' untranslated region are presented in FIG. 10.

FIG. 10 thus provides the primary structure (amino acid sequence) of rat GlcNAc T-V as including 740 specified amino acid residues (estimated M.W.=84,561). Six sites for possible N-linked glycosylation of the mature rat GlcNAc T-V polypeptide are marked in FIG. 10 with asterisks.

EXAMPLE 9

Southern Hybridizations

Appropriate amounts of rat mammary tumor genomic DNA and rat liver genomic DNA were digested in parallel reactions with restriction enzymes (BglII, NcoI, and NcoI/XhaI and BamHI/BglII) according to the instructions of the suppliers. Restriction fragments were then separated by agarose gel electrophoresis (1.0% agarose, Tris-Acetate-EDTA buffer).

The gels were then stained with ethidium bromide, excess stain was removed by soaking in TAE buffer, and the gels were photographed. The DNA in the gels was then depurinated by soaking in 0.25N HCl for 10 min with agitation.

Prior to transfer to nitrocellulose, the DNA was denatured by soaking the gels in 0.5N NaOH, 1.5M NaCl for 30 min. The nitrocellulose was soaked in double distilled water for 20–30 min, and then in 10×SSC for 20–30 min. The gel was rinsed with double distilled water and the base was neutralized by soaking the gel in 0.5M Tris-HCl (pH 7.4), 3M NaCl for 30 min.

The DNA bands in the treated gel were then blotted to the nitrocellulose by capillary transfer in 10×SSC overnight at room temperature. The positions of the wells and the orientation of the gel were marked on the nitrocellulose with a #1 pencil.

The nitrocellulose sheet was the rinsed in 4×SSC, air dried for 30 min, and baked in a vacuum oven at 80° C. for 2 hr (until thoroughly dried).

The nitrocellulose was washed with prehybridization solution for 4 hr at 42° C. Hybridization was them carried out in an overnight incubation using an approximately 200 bp amplimer probe which was random-hexamer labeled with [$\alpha$-$^{32}$P]-CTP (See Sambrook et al. (eds.) (1989) supra). The approximately 200 bp amplimer was made in a Taq polymerase reaction with Primer 1 (SEQ ID NO:5) and AntiPrimer 2 (SEQ ID NO:8) as described herein. The nitrocellulose was then washed twice with 2×SSC, 0.2% SDS at 50° C. for 30 min each time.

The hybridized nitrocellulose was then placed on X-ray film with an intensifying screen and held overnight at −80 C. to expose the film.

EXAMPLE 10

Isolation of Partial Mouse and Human sequences for Glc NAc T-V by PCR

PCR was carried out according to standard methods to determine whether Primers 1 and 2 could amplify a specific product from two cell lines (mouse lymphoma BW5147 and rat mammary tumor Mat C1 cells).

Total RNA and poly(A)+ RNA was isolated from each cell line, and used as to generate cDNA using reverse transcriptase. These cDNA preparations served as template in parallel PCR reactions as follows:

10–50 ng template cDNA

5 μl 10×Taq buffer (Mg-free)

3 μl 25 mM MgCl$_2$

1 μl dNTP mix (10 mM each)

1 μl 30 μM Primer 1

1 μl 30 μM Primer 2

38 μl sterile water 0.5 μl Taq polymerase

Each reaction was overlayered with oil and then placed in a thermal cycler apparatus with the following temperature regime:

| | |
|---|---|
| 5 min | 94° C. |
| 1 min | 94° C. |
| 1 min | 55° C. |
| 2 min | 72° C. |
| 10 min | 72° C. |

35–41 cycles (for the middle three steps)

The reaction products were then separated by agarose gel electrophoresis (2% agarose).

EXAMPLE 11

A. Transient Expression of Rat GlcNAc T-V in COS-7 Cells

The entire approximately 4.8 kb cDNA insert from one rat GlcNAc T-V clone described in Example 8, Part D was ligated into an SalI- and NotI-digested pJT-2 plasmid expression vector (Wen et al. (1992) Cell 69:559–572). COS-7 cells (CRL 1651, American Type Culture Collection, Rockville, Md.) were transfected with the pJT-2 plasmid alone or with pJT-2 plasmid containing the rat GlcNAc T-V cDNA insert by electroporation as follows: $4 \times 10^6$ cells in 0.8 ml of DMEM (Dulbecco's Modified Minimal Medium, Gibco, Grand Island, N.Y.) and 7.5% FBS (Fetal Bovine Serum, Bocknek, Ltd.) were transferred to a 0.4 cm cuvette and mixed with 10 µg of plasmid DNA in 10 µl of water. Electroporation was performed at room temperature at 1600 volts and 25 µF using a Gene Pulser apparatus (Bio-Rad Laboratories, Hercules, Calif.) with the pulse controller unit set at 200 ohms (Wen et al. (1988) supra). The cells were then diluted into approximately 40 ml of DMEM, 7.5% FBS and transferred to 100 mm culture dishes. After a 17 hr incubation at 37° C., the medium was replaced and incubation continued for an additional 51 hr or 75 hr.

B. Preparation of COS-7 Cells for GlcNAc T-V Activity Assay

The medium from each COS-7 plasmid transfected plate was removed and the cells were rinsed with phosphate-buffered saline (PBS). Cell scrapers were used to collect the cells, which were placed in tubes, diluted with PBS and centrifuged to pellet the cells. After the PBS had been aspirated, the cell pellet was subjected to quick freezing by immersion of the tube in liquid nitrogen. The cells were kept frozen on dry ice until resuspended in buffer for analysis by radiochemical assay and ELISA.

C. Assay of GlcNAc T-V Activity

Cell pellets were resuspended in 20 µl MES (pH 6.0) 150 mM NaCl buffer and disrupted by sonication. The protein content of each extract was determined as described in Example 4. GlcNAc T-V activity was then determined in radiochemical and ELISA assays.

The radiochemical assay uses a synthetic trisaccharide acceptor molecule (Srivastava et al. (1988) supra; Pierce et al. (1987) supra; Arango and Pierce (1988) supra; Palcic et al. (1988) Glycoconjugate J. 5:49–63; Pierce and Arango (1986) J. Biol. Chem. 261:10772–10277; Crawely et al. (1990) Anal. Biochem. 185:112–117). A typical assay mixture contains the following reagents dried under vacuum in a 1.5 ml centrifuge tube: $10^6$ cpm of UDP-[$^3$H]-GlcNAc (25 cpm/pmol), and 1 mM of the synthetic acceptor in a total volume of 0.01 ml. To initiate the reaction, 0.01 ml of cell extract, typically containing about 30 µg protein, in a buffer containing 50 mM MES (pH 6.0) and 1% Surfact-Amps (Triton) X-100, was added to the assay tube and incubated at 37 C. several hours (e.g., about 7 hrs). To terminate the assay, 0.5 ml H$_2$O was added to each tube, vortexed to mix thoroughly, and then contents of the tubes were centrifuged. Radiolabeled product was separated from unincorporated substrate by virtue of its hydrophobic moiety by C-18 chromatography. Each supernatant was then loaded onto a pellicular C-18 Sep Pak column which had previously been activated with methanol and pre-equilibrated with water. The column was then washed with 200 ml H$_2$O to remove water-soluble radioactivity resulting from unreacted substrate and breakdown products. The radiolabeled product was then eluted with 100% methanol, and radioactivity was measured by liquid scintillation counting. All assays were conducted at least in duplicate for two time points and the results were averaged. The variation between the values from duplicate assays did not exceed plus or minus 5%, and typically were less than plus or minus 2% of the averaged value.

The ELISA assay for GlcNAc T-V activity allows the detection of femtomole amounts of assay product, and the assay range covers a $10_6$-fold range of GlcNAc T-V activity. This assay utilizes unlabeled sugar nucleotide, the trisaccharide acceptor coupled to bovine serum albumin (BSA), and a rabbit polyclonal antibody specific for the tetrasaccharide-BSA product of the reaction. In order to determine GlcNAc T-V activity, standard calibration curves must be generated in each assay using known amounts of GlcNAc T-V, as measured in the radiochemical assay, and then absorbance in a test sample must be correlated with a particular specific activity by comparison to the standard curve.

An alternate approach to demonstrate that the full-length cDNA clone isolated does encode GlcNAc T-V, the coding sequence is fused to the N-terminal Protein A coding sequence as described in Larsen et al. (1989) Proc. Natl. Acad. Sci. USA 86:8227–8231. The resultant recombinant plasmid is then introduced into mammalian cells such that cells which have incorporated the cDNA sequences survive in culture. Because the fusion protein contains the N-terminal sequences of Protein A, the fusion protein is directed to the secretion pathway and released from the cells. After removal of the cells by centrifugation, the culture medium is assayed for GlcNAc T-V activity as described herein. A portion of the cell-free medium is chromatographed over an IgG column to which the N-terminal Protein A sequences bind, causing GlcNAc T-V activity to be retained on the column.

A second alternative approach for confirming that the cDNA isolated does encode GlcNAc T-V is to insert the complete cDNA into a vector under the control of regulatory sequences which will allow expression in the chosen mammalian host cells. The host cell chosen is a GlcNAc T-V-deficient variant of the mouse lymphoma BW5147 cell line, which variant is PHA2.1; this variant cell line is described in Cummings et al. (1982) J. Biol. Chem. 257:13421–13427. An alternative GlcNAc T-V-deficient cell line is the Lec4 variant of CHO cells, described by Stanley, P. (1983) Methods Enzymol. 96:157–184. Both variant cells lines were selected for growth in the presence of the cytotoxic lectin L-phyto-hemagglutinin, which binds to the galactosylated product of GlcNAc T-V. Expression of the cDNA sequences encoding the GlcNAc T-V restores GlcNAc T-V activity and lectin sensitivity to these variant cell lines.

The use of any one or more of the foregoing approaches provides confirmation that GlcNAc T-V is cloned as cDNA.

We claim:

1. An isolated DNA molecule consisting of a nucleotide sequence encoding a polypeptide having N-acetylglucosaminyl transferase V activity, said nucleotide sequence having at least 70% nucleotide sequence homology with a nucleotide sequence as given in SEQ ID NO:15 from nucleotide 299 to nucleotide 2521, said nucleotide sequence having been derived from rat, wherein said encoded polypeptide has an amino acid sequence as given in SEQ ID NO:16.

2. The DNA molecule of claim 1 wherein said nucleotide sequence is as given in SEQ ID NO:15, from nucleotide 299 to nucleotide 2521.

3. A DNA molecule comprising the DNA sequence of claim 1 and further comprising an exogenous nucleotide sequence.

4. The DNA molecule of claim 3 wherein said exogenous nucleotide sequence is an expression vector.

5. A transformed or transfected host cell comprising the DNA sequence of claim 4.

6. The transformed or transfected cell of claim 5 wherein said cell is a bacterial cell.

7. The transformed or transfected cell of claim 6 wherein said bacterial cell is *Escherichia coli*.

8. The transformed or transfected cell of claim 5, wherein said cell is a mammalian cell.

9. The transformed or transfected cell of claim 5, wherein said nucleotide sequence is as given in SEQ ID NO:15, from nucleotide 299 to nucleotide 2521.

10. The transformed or transfected cell of claim 9, wherein said cell is a COS-7 cell.

11. A method of producing a polypeptide having N-acetylglucosaminyltransferase V activity, said method comprising the steps of:

(a) operably linking a nucleotide sequence encoding a polypeptide, said polypeptide having N-acetylglucosaminyl transferase V activity and an amino acid sequence as given in SEQ ID NO:16, to an expression control sequence to form a GlcNAc T-V expression cassette, said nucleotide sequence being derived from rat;

(b) transforming or transfecting a cell to contain the GlcNAc T-V expression cassette of step (a) to form a GlcNAc T-V recombinant cell; and (c) culturing the GlcNAc T-V cell of step (b) under conditions appropriate for expression of said GlcNAc T-V expression cassette, whereby said nucleotide sequence directs the expression of a polypeptide having GlcNAc T-V activity.

12. The method of claim 11 wherein said nucleotide sequence is as given in SEQ ID NO:15, from nucleotide 299 to nucleotide 2521.

13. An isolated DNA molecule consisting of a nucleotide sequence encoding a polypeptide having N-acetylglucosaminyl transferase V activity, said nucleotide sequence having been derived from mouse, wherein said nucleotide sequence encoding N-acetylglucosaminyl transferase V activity comprises the nucleotide sequence as given in SEQ ID NO:17.

\* \* \* \* \*

UNITED STATES PATENT AND TRADEMARK OFFICE
CERTIFICATE OF CORRECTION

PATENT NO. : 5,602,003

DATED : February 11, 1997

INVENTOR(S) : Pierce et al.

It is certified that error appears in the above-identified patent and that said Letters Patent is hereby corrected as shown below:

Title page item [73], please add --and Amgen, Inc., Thousand Oaks, Ca-- after "University of Georgia Research Foundation, Inc., Athens, Ga."

Signed and Sealed this

Second Day of March, 1999

Attest:

Q. TODD DICKINSON

*Attesting Officer*     Acting Commissioner of Patents and Trademarks

SEQUENCE LISTING ( 1 ) GENERAL INFORMATION:

( i i i ) NUMBER OF SEQUENCES: 19

( 2 ) INFORMATION FOR SEQ ID NO:1:

( i ) SEQUENCE CHARACTERISTICS:
( A ) LENGTH: 12 amino acids
( B ) TYPE: amino acid
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:1:

Asn Thr Asp Phe Phe Ile Gly Lys Pro Thr Leu Arg
1               5                   10

( 2 ) INFORMATION FOR SEQ ID NO:2:

( i ) SEQUENCE CHARACTERISTICS:
( A ) LENGTH: 16 amino acids
( B ) TYPE: amino acid
( D ) TOPOLOGY: linear ( i i ) MOLECULE TYPE: peptide ( i i i ) HYPOTHETICAL: NO ( v ) FRAGMENT TYPE: internal ( x i ) SEQUENCE DESCRIPTION: SEQ ID NO:2:

Ala Ile Leu Asn Gln Lys Ile Glu Pro Tyr Met Pro Tyr Glu Phe Thr
1               5                   10                  15

( 2 ) INFORMATION FOR SEQ ID NO:3:

( i ) SEQUENCE CHARACTERISTICS:
( A ) LENGTH: 12 amino acids
( B ) TYPE: amino acid
( D ) TOPOLOGY: linear ( i i ) MOLECULE TYPE: peptide ( i i i ) HYPOTHETICAL: NO ( v ) FRAGMENT TYPE: internal ( x i ) SEQUENCE DESCRIPTION: SEQ ID NO:3:

Val Leu Asp Ser Phe Gly Thr Glu Pro Glu Phe Asn
1               5                   10

( 2 ) INFORMATION FOR SEQ ID NO:4:

( i ) SEQUENCE CHARACTERISTICS:
( A ) LENGTH: 10 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( v ) FRAGMENT TYPE: internal ( i x ) FEATURE:
  ( A ) NAME/KEY: Region
  ( B ) LOCATION: 1..10
  ( D ) OTHER INFORMATION: /label= UNCERTAIN
   / note= "AMINO ACIDS AT POSITIONS 4, 7 AND 9 WERE IDENTIFIED WITH UNCERTAINTY"

( x i ) SEQUENCE DESCRIPTION: SEQ ID NO:4:

Ser Asp Pro Cys Tyr Ala Asp Tyr Glu Val
1     5       10

( 2 ) INFORMATION FOR SEQ ID NO:5:

( i ) SEQUENCE CHARACTERISTICS:
  ( A ) LENGTH: 29 base pairs
  ( B ) TYPE: nucleic acid
  ( C ) STRANDEDNESS: single
  ( D ) TOPOLOGY: linear ( i i ) MOLECULE TYPE: DNA (other)

( i i i ) HYPOTHETICAL: NO ( i x ) FEATURE:
  ( A ) NAME/KEY: misc_difference
  ( B ) LOCATION: replace(1..22, "")
  ( D ) OTHER INFORMATION: /standard_name= "N IS INOSINE AT POSITIONS 6 AND 21"

( x i ) SEQUENCE DESCRIPTION: SEQ ID NO:5:

AAYACNGAYT TYTTYATHGG NAARCCNAC           29

( 2 ) INFORMATION FOR SEQ ID NO:6:

( i ) SEQUENCE CHARACTERISTICS:
  ( A ) LENGTH: 29 base pairs
  ( B ) TYPE: nucleic acid
  ( C ) STRANDEDNESS: single
  ( D ) TOPOLOGY: linear ( i i ) MOLECULE TYPE: DNA (other)

( i i i ) HYPOTHETICAL: NO ( i x ) FEATURE:
  ( A ) NAME/KEY: misc_difference
  ( B ) LOCATION: replace(1..29, "")
  ( D ) OTHER INFORMATION: /standard_name= "N IS INOSINE AT POSITIONS 3, 9 AND 24."

( x i ) SEQUENCE DESCRIPTION: SEQ ID NO:6:

GTNGGYTTNC CDATRAARAA RTCNGTRTT          29

( 2 ) INFORMATION FOR SEQ ID NO:7:

( i ) SEQUENCE CHARACTERISTICS:
  ( A ) LENGTH: 29 base pairs
  ( B ) TYPE: nucleic acid
  ( C ) STRANDEDNESS: single
  ( D ) TOPOLOGY: linear ( i i ) MOLECULE TYPE: DNA (other)

( i i i ) HYPOTHETICAL: NO ( i x ) FEATURE:
  ( A ) NAME/KEY: misc_difference
  ( B ) LOCATION: replace(1..29, "")
  ( D ) OTHER INFORMATION: /standard_name= "I IS INOSINE AT POSITIONS 3, 9 AND 24."

( x i ) SEQUENCE DESCRIPTION: SEQ ID NO:7:

ATHGARCCNT AYATGCCNTA YGARTTYAC                                    29

(2) INFORMATION FOR SEQ ID NO:8:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (other)

(iii) HYPOTHETICAL: NO (ix) FEATURE:
        (A) NAME/KEY: misc_difference
        (B) LOCATION: replace(1..16, "")
        (D) OTHER INFORMATION: /standard_name= "I IS INOSINE AT
            POSITIONS 6 AND 15"

(xi) SEQUENCE DESCRIPTION: SEQ ID NO:8:

TCRTANGGCA TRTANGGYTC DATYTTYTG                                    29

(2) INFORMATION FOR SEQ ID NO:9:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (other)

(iii) HYPOTHETICAL: NO (xi) SEQUENCE DESCRIPTION: SEQ ID NO:9:

GGGCCGATGA AGACTTCTGC G                                            21

(2) INFORMATION FOR SEQ ID NO:10:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (other)

(iii) HYPOTHETICAL: NO (xi) SEQUENCE DESCRIPTION: SEQ ID NO:10:

GGGCTACTTC CTCTCGGTTA TTGAG                                        25

(2) INFORMATION FOR SEQ ID NO:11:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (other)

(iii) HYPOTHETICAL: NO (xi) SEQUENCE DESCRIPTION: SEQ ID NO:11:

GCTCTAATAC GACTCACTAT AGG                                          23

(2) INFORMATION FOR SEQ ID NO:12:

(i) SEQUENCE CHARACTERISTICS:

( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (other)

( i i i ) HYPOTHETICAL: NO ( x i ) SEQUENCE DESCRIPTION: SEQ ID NO:12:

GGGTACGTGT GAATGATATC CAGGTAG 27

( 2 ) INFORMATION FOR SEQ ID NO:13:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA (other)

( i i i ) HYPOTHETICAL: NO ( x i ) SEQUENCE DESCRIPTION: SEQ ID NO:13:

CCCGTCGACG AGAGCCAAGG GAATGGTAC 29

( 2 ) INFORMATION FOR SEQ ID NO:14:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (other)

( i i i ) HYPOTHETICAL: NO ( x i ) SEQUENCE DESCRIPTION: SEQ ID NO:14:

CCCAGCAGGT ACAGAGATGT G 21

( 2 ) INFORMATION FOR SEQ ID NO:15:

( i ) SEQUENCE CHARACTERISTICS:
        ( A ) LENGTH: 2624 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( i x ) FEATURE:
        ( A ) NAME/KEY: CDS
        ( B ) LOCATION: 299..2521

( x i ) SEQUENCE DESCRIPTION: SEQ ID NO:15:

TGACCCCGCT CCTGGCTGTG CCTGGGACCC CAGTTCCCAG GAGCACGGTT GCAGGAGAGT 60

GACCCCGACT GCTACTGATG GTGCTTCTGC TGCTCCTCTA CTAGCAGGAG TGACTCCTAC 120

CCAGAAGTGG ACTTGGAGGA GGGTCCGTTA GACCATCAGA ATGGAAGCCC GACAAGCAAG 180

TCAGCTGACT CAGGAACCAG AGTGAGGGCC ACGCACTCTC CGCCCCAGCC TGCACCATGA 240

ACTTGCCTTC CCCTTCTGCT TGTTGAGAGC CAAGGGAATG GTACATTACT AGAGAGAG 298

ATG GCT TTC TTT TCT CCC TGG AAG TTG TCC TCT CAG AAG CTG GGC TTT 346
Met Ala Phe Phe Ser Pro Trp Lys Leu Ser Ser Gln Lys Leu Gly Phe

|   |   |   |   |   |   |   |   |   |   |   |   |   |   |   |   |      |
|---|---|---|---|---|---|---|---|---|---|---|---|---|---|---|---|------|
| 1 |   |   |   | 5 |   |   |   |   | 10 |   |   |   |   | 15 |   |   |

| TTC | TTG | GTG | ACT | TTT | GGC | TTC | ATA | TGG | GGG | ATG | ATG | CTT | CTA | CAC | TTC | 394 |
| Phe | Leu | Val | Thr | Phe | Gly | Phe | Ile | Trp | Gly | Met | Met | Leu | Leu | His | Phe |     |
|     |     |     | 20  |     |     |     |     | 25  |     |     |     |     | 30  |     |     |     |

| ACC | ATC | CAG | CAG | CGA | ACT | CAG | CCT | GAG | AGC | AGC | TCC | ATG | TTG | CGG | GAG | 442 |
| Thr | Ile | Gln | Gln | Arg | Thr | Gln | Pro | Glu | Ser | Ser | Ser | Met | Leu | Arg | Glu |     |
|     |     |     | 35  |     |     |     | 40  |     |     |     |     | 45  |     |     |     |     |

| CAA | ATC | CTT | GAC | CTC | AGC | AAA | AGG | TAC | ATT | AAG | GCA | CTG | GCA | GAA | GAG | 490 |
| Gln | Ile | Leu | Asp | Leu | Ser | Lys | Arg | Tyr | Ile | Lys | Ala | Leu | Ala | Glu | Glu |     |
|     |     | 50  |     |     |     |     | 55  |     |     |     |     | 60  |     |     |     |     |

| AAC | AGG | AAC | GTG | GTG | GAT | GGC | CCG | TAT | GCC | GGT | GTC | ATG | ACA | GCC | TAT | 538 |
| Asn | Arg | Asn | Val | Val | Asp | Gly | Pro | Tyr | Ala | Gly | Val | Met | Thr | Ala | Tyr |     |
| 65  |     |     |     |     | 70  |     |     |     |     | 75  |     |     |     |     | 80  |     |

| GAT | CTG | AAG | AAA | ACG | CTC | GCC | GTG | CTG | CTG | GAT | AAC | ATC | TTG | CAG | CGC | 586 |
| Asp | Leu | Lys | Lys | Thr | Leu | Ala | Val | Leu | Leu | Asp | Asn | Ile | Leu | Gln | Arg |     |
|     |     |     |     | 85  |     |     |     |     | 90  |     |     |     |     | 95  |     |     |

| ATC | GGC | AAG | CTG | GAG | TCC | AAG | GTG | GAC | AAT | CTT | GTC | AAC | GGC | ACA | GGA | 634 |
| Ile | Gly | Lys | Leu | Glu | Ser | Lys | Val | Asp | Asn | Leu | Val | Asn | Gly | Thr | Gly |     |
|     |     |     |     | 100 |     |     |     |     | 105 |     |     |     |     | 110 |     |     |

| GCG | AAT | TCT | ACC | AAC | TCC | ACC | ACG | GCT | GTC | CCC | AGC | TTG | GTG | TCA | CTG | 682 |
| Ala | Asn | Ser | Thr | Asn | Ser | Thr | Thr | Ala | Val | Pro | Ser | Leu | Val | Ser | Leu |     |
|     |     | 115 |     |     |     |     | 120 |     |     |     |     | 125 |     |     |     |     |

| GAG | AAA | ATT | AAT | GTG | GCA | GAT | ATC | ATT | AAT | GGA | GTT | CAA | GAA | AAA | TGT | 730 |
| Glu | Lys | Ile | Asn | Val | Ala | Asp | Ile | Ile | Asn | Gly | Val | Gln | Glu | Lys | Cys |     |
|     | 130 |     |     |     |     | 135 |     |     |     |     | 140 |     |     |     |     |     |

| GTA | TTG | CCT | CCT | ATG | GAT | GGC | TAC | CCC | CAC | TGC | GAG | GGG | AAA | ATC | AAG | 778 |
| Val | Leu | Pro | Pro | Met | Asp | Gly | Tyr | Pro | His | Cys | Glu | Gly | Lys | Ile | Lys |     |
| 145 |     |     |     |     | 150 |     |     |     |     | 155 |     |     |     |     | 160 |     |

| TGG | ATG | AAA | GAC | ATG | TGG | CGG | TCA | GAC | CCC | TGC | TAC | GCA | GAC | TAT | GGA | 826 |
| Trp | Met | Lys | Asp | Met | Trp | Arg | Ser | Asp | Pro | Cys | Tyr | Ala | Asp | Tyr | Gly |     |
|     |     |     |     | 165 |     |     |     |     | 170 |     |     |     |     | 175 |     |     |

| GTG | GAC | GGG | ACC | TCC | TGC | TCC | TTT | TTT | ATT | TAC | CTC | AGT | GAG | GTT | GAA | 874 |
| Val | Asp | Gly | Thr | Ser | Cys | Ser | Phe | Phe | Ile | Tyr | Leu | Ser | Glu | Val | Glu |     |
|     |     |     | 180 |     |     |     |     | 185 |     |     |     |     | 190 |     |     |     |

| AAT | TGG | TGT | CCT | CGT | TTA | CCT | TGG | AGA | GCA | AAA | AAT | CCC | TAT | GAA | GAA | 922 |
| Asn | Trp | Cys | Pro | Arg | Leu | Pro | Trp | Arg | Ala | Lys | Asn | Pro | Tyr | Glu | Glu |     |
|     |     | 195 |     |     |     |     | 200 |     |     |     |     | 205 |     |     |     |     |

| GCT | GAC | CAT | AAC | TCA | TTG | GCA | GAA | ATC | CGC | ACG | GAT | TTT | AAC | ATT | CTC | 970 |
| Ala | Asp | His | Asn | Ser | Leu | Ala | Glu | Ile | Arg | Thr | Asp | Phe | Asn | Ile | Leu |     |
| 210 |     |     |     |     | 215 |     |     |     |     | 220 |     |     |     |     |     |     |

| TAC | GGC | ATG | ATG | AAG | AAG | CAT | GAG | GAG | TTC | CGG | TGG | ATG | AGA | CTT | CGG | 1018 |
| Tyr | Gly | Met | Met | Lys | Lys | His | Glu | Glu | Phe | Arg | Trp | Met | Arg | Leu | Arg |     |
| 225 |     |     |     |     | 230 |     |     |     |     | 235 |     |     |     |     | 240 |     |

| ATC | CGG | CGA | ATG | GCT | GAT | GCA | TGG | ATC | CAA | GCA | ATC | AAG | TCT | CTG | GCA | 1066 |
| Ile | Arg | Arg | Met | Ala | Asp | Ala | Trp | Ile | Gln | Ala | Ile | Lys | Ser | Leu | Ala |     |
|     |     |     |     | 245 |     |     |     |     | 250 |     |     |     |     | 255 |     |     |

| GAG | AAA | CAA | AAC | CTA | GAG | AAG | AGG | AAA | CGG | AAG | AAA | ATC | CTT | GTT | CAC | 1114 |
| Glu | Lys | Gln | Asn | Leu | Glu | Lys | Arg | Lys | Arg | Lys | Lys | Ile | Leu | Val | His |     |
|     |     |     | 260 |     |     |     |     | 265 |     |     |     |     | 270 |     |     |     |

| CTG | GGG | CTC | CTG | ACC | AAG | GAA | TCA | GGC | TTC | AAG | ATT | GCA | GAG | ACA | GCA | 1162 |
| Leu | Gly | Leu | Leu | Thr | Lys | Glu | Ser | Gly | Phe | Lys | Ile | Ala | Glu | Thr | Ala |     |
|     |     | 275 |     |     |     |     | 280 |     |     |     |     | 285 |     |     |     |     |

| TTC | AGC | GGT | GGC | CCT | CTC | GGC | GAG | CTC | GTT | CAG | TGG | AGT | GAC | TTA | ATC | 1210 |
| Phe | Ser | Gly | Gly | Pro | Leu | Gly | Glu | Leu | Val | Gln | Trp | Ser | Asp | Leu | Ile |     |
|     | 290 |     |     |     |     | 295 |     |     |     |     | 300 |     |     |     |     |     |

| ACA | TCT | CTG | TAC | CTG | CTG | GGC | CAT | GAC | ATC | CGC | ATC | TCA | GCC | TCG | CTG | 1258 |
| Thr | Ser | Leu | Tyr | Leu | Leu | Gly | His | Asp | Ile | Arg | Ile | Ser | Ala | Ser | Leu |     |
| 305 |     |     |     |     | 310 |     |     |     |     | 315 |     |     |     |     | 320 |     |

| GCT | GAG | CTC | AAG | GAG | ATT | ATG | AAG | AAG | GTT | GTT | GGA | AAC | CGG | TCT | GGC | 1306 |
| Ala | Glu | Leu | Lys | Glu | Ile | Met | Lys | Lys | Val | Val | Gly | Asn | Arg | Ser | Gly |     |

|  |  |  |  |  |  |  |  |  |  |  |  |  |  |  |  |  |
|---|---|---|---|---|---|---|---|---|---|---|---|---|---|---|---|---|
|  |  |  |  | 325 |  |  |  |  | 330 |  |  |  |  | 335 |  |  |
| TGT Cys | CCA Pro | ACT Thr | GTA Val 340 | GGA Gly | GAC Asp | AGA Arg | ATC Ile | GTT Val 345 | GAG Glu | CTT Leu | ATT Ile | TAT Tyr | ATC Ile 350 | GAT Asp | ATT Ile | 1354 |
| GTG Val | GGA Gly | CTT Leu 355 | GCT Ala | CAA Gln | TTC Phe | AAG Lys | AAA Lys 360 | ACG Thr | CTA Leu | GGA Gly | CCA Pro | TCC Ser 365 | TGG Trp | GTT Val | CAT His | 1402 |
| TAC Tyr | CAG Gln 370 | TGC Cys | ATG Met | CTC Leu | CGG Arg | GTG Val 375 | CTG Leu | GAC Asp | TCC Ser | TTT Phe | GGA Gly 380 | ACA Thr | GAA Glu | CCT Pro | GAG Glu | 1450 |
| TTC Phe 385 | AAT Asn | CAC His | GCA Ala | AGT Ser | TAC Tyr 390 | GCC Ala | CAG Gln | TCG Ser | AAA Lys | GGC Gly 395 | CAC His | AAG Lys | ACC Thr | CCC Pro | TGG Trp 400 | 1498 |
| GGA Gly | AAG Lys | TGG Trp | AAT Asn | CTG Leu 405 | AAC Asn | CCG Pro | CAA Gln | CAG Gln | TTT Phe 410 | TAC Tyr | ACC Thr | ATG Met | TTC Phe | CCT Pro 415 | CAT His | 1546 |
| ACC Thr | CCA Pro | GAC Asp | AAC Asn | AGC Ser 420 | TTT Phe | CTG Leu | GGC Gly | TTC Phe | GTG Val 425 | GTC Val | GAG Glu | CAG Gln | CAC His | CTG Leu 430 | AAC Asn | 1594 |
| TCC Ser | AGC Ser | GAC Asp 435 | ATC Ile | CAC His | CAC His | ATT Ile | AAC Asn 440 | GAG Glu | ATC Ile | AAA Lys | AGG Arg | CAG Gln 445 | AAC Asn | CAG Gln | TCC Ser | 1642 |
| CTT Leu | GTG Val 450 | TAT Tyr | GGC Gly | AAA Lys | GTG Val | GAT Asp 455 | AGT Ser | TTC Phe | TGG Trp | AAG Lys | AAT Asn 460 | AAG Lys | AAG Lys | ATC Ile | TAC Tyr | 1690 |
| TTG Leu 465 | GAC Asp | ATC Ile | ATT Ile | CAC His | ACG Thr 470 | TAC Tyr | ATG Met | GAA Glu | GTG Val | CAC His 475 | GCC Ala | ACT Thr | GTT Val | TAC Tyr | GGC Gly 480 | 1738 |
| TCC Ser | AGT Ser | ACC Thr | AAG Lys | AAC Asn 485 | ATC Ile | CCC Pro | AGT Ser | TAC Tyr | GTG Val 490 | AAA Lys | AAC Asn | CAT His | GGC Gly | ATT Ile 495 | CTC Leu | 1786 |
| AGC Ser | GGC Gly | CGT Arg | GAC Asp 500 | CTA Leu | CAG Gln | TTT Phe | CTT Leu | CTC Leu 505 | CGG Arg | GAA Glu | ACC Thr | AAG Lys | CTT Leu 510 | TTT Phe | GTT Val | 1834 |
| GGG Gly | CTT Leu | GGA Gly 515 | TTC Phe | CCT Pro | TAT Tyr | GAA Glu | GGT Gly 520 | CCA Pro | GCT Ala | CCC Pro | CTG Leu | GAA Glu 525 | GCC Ala | ATC Ile | GCG Ala | 1882 |
| AAT Asn | GGA Gly 530 | TGT Cys | GCT Ala | TTC Phe | CTG Leu | AAC Asn 535 | CCC Pro | AAG Lys | TTC Phe | AAC Asn | CCT Pro 540 | CCT Pro | AAA Lys | AGC Ser | AGC Ser | 1930 |
| AAA Lys 545 | AAC Asn | ACA Thr | GAC Asp | TTC Phe | TTC Phe 550 | ATT Ile | GGC Gly | AAG Lys | CCA Pro | ACA Thr 555 | CTG Leu | AGA Arg | GAG Glu | CTC Leu | ACA Thr 560 | 1978 |
| TCC Ser | CAG Gln | CAC His | CCG Pro | TAC Tyr 565 | GCA Ala | GAA Glu | GTC Val | TTC Phe | ATC Ile 570 | GGC Gly | CGG Arg | CCA Pro | CAC His | GTC Val 575 | TGG Trp | 2026 |
| ACC Thr | GTG Val | GAC Asp | CTC Leu 580 | AAT Asn | AAC Asn | CGA Arg | GAG Glu | GAA Glu 585 | GTA Val | GAA Glu | GAC Asp | GCA Ala | GTA Val 590 | AAA Lys | GCC Ala | 2074 |
| ATC Ile | TTA Leu | AAC Asn 595 | CAG Gln | AAG Lys | ATT Ile | GAG Glu | CCG Pro 600 | TAT Tyr | ATG Met | CCA Pro | TAT Tyr | GAG Glu 605 | TTC Phe | ACA Thr | TGT Cys | 2122 |
| GAA Glu | GGC Gly 610 | ATG Met | CTG Leu | CAG Gln | AGA Arg | ATC Ile 615 | AAC Asn | GCT Ala | TTC Phe | ATC Ile | GAG Glu 620 | AAA Lys | CAG Gln | GAC Asp | TTC Phe | 2170 |
| TGC Cys 625 | CAC His | GGC Gly | CAA Gln | GTG Val | ATG Met 630 | TGG Trp | CCG Pro | CCC Pro | CTT Leu | AGC Ser 635 | GCC Ala | CTG Leu | CAG Gln | GTG Val | AAG Lys 640 | 2218 |
| CTG Leu | GCT Ala | GAG Glu | CCC Pro | GGG Gly | CAG Gln | TCC Ser | TGC Cys | AAA Lys | CAG Gln | GTG Val | TGC Cys | CAG Gln | GAG Glu | AGC Ser | CAG Gln | 2266 |

|  |  |  |  |  |  |  |  |  |  |  |  |  |  |  | |
|---|---|---|---|---|---|---|---|---|---|---|---|---|---|---|---|
|  |  |  | 645 |  |  |  |  | 650 |  |  |  |  | 655 |  | |
| CTC | ATC | TGC | GAG | CCG | TCC | TTC | TTC | CAG | CAC | CTC | AAC | AAG | GAA | AAG | GAC | 2314 |
| Leu | Ile | Cys | Glu | Pro | Ser | Phe | Phe | Gln | His | Leu | Asn | Lys | Glu | Lys | Asp |  |
|  |  |  | 660 |  |  |  |  | 665 |  |  |  |  | 670 |  | |
| CTG | CTG | AAG | TAT | AAG | GTA | ATC | TGC | CAA | AGC | TCA | GAA | CTA | TAC | AAG | GAC | 2362 |
| Leu | Leu | Lys | Tyr | Lys | Val | Ile | Cys | Gln | Ser | Ser | Glu | Leu | Tyr | Lys | Asp |  |
|  |  | 675 |  |  |  |  | 680 |  |  |  |  | 685 |  |  | |
| ATC | CTG | GTG | CCC | TCC | TTC | TAC | CCC | AAG | AGC | AAG | CAC | TGT | GTG | TTC | CAA | 2410 |
| Ile | Leu | Val | Pro | Ser | Phe | Tyr | Pro | Lys | Ser | Lys | His | Cys | Val | Phe | Gln |  |
|  | 690 |  |  |  |  | 695 |  |  |  |  | 700 |  |  |  | |
| GGG | GAT | CTC | CTG | CTC | TTC | AGT | TGT | GCC | GGG | GCC | CAC | CCC | ACA | CAC | CAG | 2458 |
| Gly | Asp | Leu | Leu | Leu | Phe | Ser | Cys | Ala | Gly | Ala | His | Pro | Thr | His | Gln |  |
| 705 |  |  |  | 710 |  |  |  |  | 715 |  |  |  |  | 720 | |
| CGG | ATC | TGC | CCC | TGC | CGG | GAC | TTC | ATC | AAG | GGC | CAA | GTG | GCC | CTC | TGC | 2506 |
| Arg | Ile | Cys | Pro | Cys | Arg | Asp | Phe | Ile | Lys | Gly | Gln | Val | Ala | Leu | Cys |  |
|  |  |  |  | 725 |  |  |  |  | 730 |  |  |  |  | 735 | |
| AAA | GAC | TGC | CTA | TAGCATAGCC | | | ACCCTGGATT | | | CATTCAGATG | | | GGAAAGACGT | | | 2558 |
| Lys | Asp | Cys | Leu |  |  |  |  |  |  |  |  |  |  |  | |
|  |  |  | 740 |  |  |  |  |  |  |  |  |  |  |  | |

GGCTCCGCTG GGCAGGGCCG AGGGGCTGAA AGACAGTCAG GGACTCTGAC CAGAGCCTGA    2618

AATCTT    2624

( 2 ) INFORMATION FOR SEQ ID NO:16:

( i ) SEQUENCE CHARACTERISTICS:
        ( A ) LENGTH: 740 amino acids
        ( B ) TYPE: amino acid
        ( D ) TOPOLOGY: linear ( i i ) MOLECULE TYPE: protein ( x i ) SEQUENCE DESCRIPTION: SEQ ID NO:16:

| Met | Ala | Phe | Phe | Ser | Pro | Trp | Lys | Leu | Ser | Ser | Gln | Lys | Leu | Gly | Phe |
|---|---|---|---|---|---|---|---|---|---|---|---|---|---|---|---|
| 1 |  |  |  | 5 |  |  |  |  | 10 |  |  |  |  | 15 | |
| Phe | Leu | Val | Thr | Phe | Gly | Phe | Ile | Trp | Gly | Met | Met | Leu | Leu | His | Phe |
|  |  |  | 20 |  |  |  |  | 25 |  |  |  |  | 30 |  | |
| Thr | Ile | Gln | Gln | Arg | Thr | Gln | Pro | Glu | Ser | Ser | Ser | Met | Leu | Arg | Glu |
|  |  |  | 35 |  |  |  |  | 40 |  |  |  |  | 45 |  | |
| Gln | Ile | Leu | Asp | Leu | Ser | Lys | Arg | Tyr | Ile | Lys | Ala | Leu | Ala | Glu | Glu |
|  |  | 50 |  |  |  |  | 55 |  |  |  |  | 60 |  |  | |
| Asn | Arg | Asn | Val | Val | Asp | Gly | Pro | Tyr | Ala | Gly | Val | Met | Thr | Ala | Tyr |
| 65 |  |  |  |  | 70 |  |  |  |  | 75 |  |  |  |  | 80 |
| Asp | Leu | Lys | Lys | Thr | Leu | Ala | Val | Leu | Leu | Asp | Asn | Ile | Leu | Gln | Arg |
|  |  |  |  | 85 |  |  |  |  | 90 |  |  |  |  | 95 | |
| Ile | Gly | Lys | Leu | Glu | Ser | Lys | Val | Asp | Asn | Leu | Val | Asn | Gly | Thr | Gly |
|  |  |  | 100 |  |  |  |  | 105 |  |  |  |  | 110 |  | |
| Ala | Asn | Ser | Thr | Asn | Ser | Thr | Thr | Ala | Val | Pro | Ser | Leu | Val | Ser | Leu |
|  |  |  | 115 |  |  |  |  | 120 |  |  |  |  | 125 |  | |
| Glu | Lys | Ile | Asn | Val | Ala | Asp | Ile | Ile | Asn | Gly | Val | Gln | Glu | Lys | Cys |
|  | 130 |  |  |  |  | 135 |  |  |  |  | 140 |  |  |  | |
| Val | Leu | Pro | Pro | Met | Asp | Gly | Tyr | Pro | His | Cys | Glu | Gly | Lys | Ile | Lys |
| 145 |  |  |  |  | 150 |  |  |  |  | 155 |  |  |  |  | 160 |
| Trp | Met | Lys | Asp | Met | Trp | Arg | Ser | Asp | Pro | Cys | Tyr | Ala | Asp | Tyr | Gly |
|  |  |  |  | 165 |  |  |  |  | 170 |  |  |  |  | 175 | |
| Val | Asp | Gly | Thr | Ser | Cys | Ser | Phe | Phe | Ile | Tyr | Leu | Ser | Glu | Val | Glu |
|  |  |  | 180 |  |  |  |  | 185 |  |  |  |  | 190 |  | |
| Asn | Trp | Cys | Pro | Arg | Leu | Pro | Trp | Arg | Ala | Lys | Asn | Pro | Tyr | Glu | Glu |
|  |  |  | 195 |  |  |  |  | 200 |  |  |  |  | 205 |  | |

```
Ala  Asp  His  Asn  Ser  Leu  Ala  Glu  Ile  Arg  Thr  Asp  Phe  Asn  Ile  Leu
     210                 215                      220
Tyr  Gly  Met  Met  Lys  Lys  His  Glu  Glu  Phe  Arg  Trp  Met  Arg  Leu  Arg
225                      230                 235                           240
Ile  Arg  Arg  Met  Ala  Asp  Ala  Trp  Ile  Gln  Ala  Ile  Lys  Ser  Leu  Ala
               245                      250                      255
Glu  Lys  Gln  Asn  Leu  Glu  Lys  Arg  Lys  Arg  Lys  Ile  Leu  Val  His
          260                      265                      270
Leu  Gly  Leu  Leu  Thr  Lys  Glu  Ser  Gly  Phe  Lys  Ile  Ala  Glu  Thr  Ala
          275                      280                      285
Phe  Ser  Gly  Gly  Pro  Leu  Gly  Glu  Leu  Val  Gln  Trp  Ser  Asp  Leu  Ile
     290                      295                 300
Thr  Ser  Leu  Tyr  Leu  Leu  Gly  His  Asp  Ile  Arg  Ile  Ser  Ala  Ser  Leu
305                      310                 315                           320
Ala  Glu  Leu  Lys  Glu  Ile  Met  Lys  Lys  Val  Val  Gly  Asn  Arg  Ser  Gly
                    325                      330                      335
Cys  Pro  Thr  Val  Gly  Asp  Arg  Ile  Val  Glu  Leu  Ile  Tyr  Ile  Asp  Ile
               340                      345                      350
Val  Gly  Leu  Ala  Gln  Phe  Lys  Lys  Thr  Leu  Gly  Pro  Ser  Trp  Val  His
          355                      360                      365
Tyr  Gln  Cys  Met  Leu  Arg  Val  Leu  Asp  Ser  Phe  Gly  Thr  Glu  Pro  Glu
     370                      375                      380
Phe  Asn  His  Ala  Ser  Tyr  Ala  Gln  Ser  Lys  Gly  His  Lys  Thr  Pro  Trp
385                      390                      395                      400
Gly  Lys  Trp  Asn  Leu  Asn  Pro  Gln  Gln  Phe  Tyr  Thr  Met  Phe  Pro  His
               405                      410                      415
Thr  Pro  Asp  Asn  Ser  Phe  Leu  Gly  Phe  Val  Val  Glu  Gln  His  Leu  Asn
               420                      425                 430
Ser  Ser  Asp  Ile  His  His  Ile  Asn  Glu  Ile  Lys  Arg  Gln  Asn  Gln  Ser
          435                      440                      445
Leu  Val  Tyr  Gly  Lys  Val  Asp  Ser  Phe  Trp  Lys  Asn  Lys  Lys  Ile  Tyr
     450                      455                      460
Leu  Asp  Ile  Ile  His  Thr  Tyr  Met  Glu  Val  His  Ala  Thr  Val  Tyr  Gly
465                      470                      475                      480
Ser  Ser  Thr  Lys  Asn  Ile  Pro  Ser  Tyr  Val  Lys  Asn  His  Gly  Ile  Leu
               485                      490                           495
Ser  Gly  Arg  Asp  Leu  Gln  Phe  Leu  Leu  Arg  Glu  Thr  Lys  Leu  Phe  Val
               500                 505                      510
Gly  Leu  Gly  Phe  Pro  Tyr  Glu  Gly  Pro  Ala  Pro  Leu  Glu  Ala  Ile  Ala
          515                      520                 525
Asn  Gly  Cys  Ala  Phe  Leu  Asn  Pro  Lys  Phe  Asn  Pro  Pro  Lys  Ser  Ser
     530                      535                      540
Lys  Asn  Thr  Asp  Phe  Phe  Ile  Gly  Lys  Pro  Thr  Leu  Arg  Glu  Leu  Thr
545                      550                      555                      560
Ser  Gln  His  Pro  Tyr  Ala  Glu  Val  Phe  Ile  Gly  Arg  Pro  His  Val  Trp
                    565                      570                      575
Thr  Val  Asp  Leu  Asn  Asn  Arg  Glu  Glu  Val  Glu  Asp  Ala  Val  Lys  Ala
               580                      585                      590
Ile  Leu  Asn  Gln  Lys  Ile  Glu  Pro  Tyr  Met  Pro  Tyr  Glu  Phe  Thr  Cys
          595                      600                      605
Glu  Gly  Met  Leu  Gln  Arg  Ile  Asn  Ala  Phe  Ile  Glu  Lys  Gln  Asp  Phe
     610                      615                      620
Cys  His  Gly  Gln  Val  Met  Trp  Pro  Pro  Leu  Ser  Ala  Leu  Gln  Val  Lys
```

```
625                   630                   635                   640
Leu  Ala  Glu  Pro  Gly  Gln  Ser  Cys  Lys  Gln  Val  Cys  Gln  Glu  Ser  Gln
                    645                      650                      655

Leu  Ile  Cys  Glu  Pro  Ser  Phe  Phe  Gln  His  Leu  Asn  Lys  Glu  Lys  Asp
                    660                      665                      670

Leu  Leu  Lys  Tyr  Lys  Val  Ile  Cys  Gln  Ser  Ser  Glu  Leu  Tyr  Lys  Asp
               675                      680                      685

Ile  Leu  Val  Pro  Ser  Phe  Tyr  Pro  Lys  Ser  Lys  His  Cys  Val  Phe  Gln
     690                           695                 700

Gly  Asp  Leu  Leu  Leu  Phe  Ser  Cys  Ala  Gly  Ala  His  Pro  Thr  His  Gln
705                      710                      715                      720

Arg  Ile  Cys  Pro  Cys  Arg  Asp  Phe  Ile  Lys  Gly  Gln  Val  Ala  Leu  Cys
                    725                      730                      735

Lys  Asp  Cys  Leu
               740
```

( 2 ) INFORMATION FOR SEQ ID NO:17:

( i ) SEQUENCE CHARACTERISTICS:
           ( A ) LENGTH: 178 base pairs
           ( B ) TYPE: nucleic acid
           ( C ) STRANDEDNESS: double
           ( D ) TOPOLOGY: linear ( i i ) MOLECULE TYPE: DNA (other)

( i i i ) HYPOTHETICAL: NO ( x i ) SEQUENCE DESCRIPTION: SEQ ID NO:17:

```
AATACGGATT   TCTTCATCGG   GAAGCCTACA   CTGAGAGAGC   TGACATCCCA   GCATCCTTAC      60

GCAGAAGTCT   TCATCGGCCG   GCCACACGTC   TGGACTGTGG   ATCTCAATAA   CCGAGAGGAA     120

GTAGAAGATG   CAGTAAAAGC   CATCTTAAAC   CAGAAGATTG   AGCCCTATAT   GCCCTACG      178
```

( 2 ) INFORMATION FOR SEQ ID NO:18:

( i ) SEQUENCE CHARACTERISTICS:
           ( A ) LENGTH: 179 base pairs
           ( B ) TYPE: nucleic acid
           ( C ) STRANDEDNESS: double
           ( D ) TOPOLOGY: linear ( i i ) MOLECULE TYPE: DNA (other)

( i i i ) HYPOTHETICAL: NO ( x i ) SEQUENCE DESCRIPTION: SEQ ID NO:18:

```
AACACGGACT   TTTTTATCGG   GAAGCCTACA   CTGAGAGAGC   TCACATCCCA   GCACCCGTAC      60

GCAGAAGTCT   TCATCGGCCG   GCCACACGTC   TGGACCGTGG   ACCTCAATAA   CCGAGAGGAA     120

GTAGAAGACG   CAGTAAAAGC   CATCTTAAAC   CAAAAAATTG   AACCCTACAT   GCCCTACGA     179
```

( 2 ) INFORMATION FOR SEQ ID NO:19:

( i ) SEQUENCE CHARACTERISTICS:
           ( A ) LENGTH: 166 base pairs
           ( B ) TYPE: nucleic acid
           ( C ) STRANDEDNESS: double
           ( D ) TOPOLOGY: linear ( i i ) MOLECULE TYPE: DNA (other)

( i i i ) HYPOTHETICAL: NO ( x i ) SEQUENCE DESCRIPTION: SEQ ID NO:19:

| | | | | | |
|---|---|---|---|---|---|
| AACACGGATT | TCTTCATCGG | GAAACCCACA | CTGAGAGAGC | TGACATCCCA | GCATCCTTAC | 60 |
| GCAGAAGTCT | TCATCGGCCG | GCCACACGTC | TGGACTGTGG | ATCTCAATAA | CCGAGAGGAA | 120 |
| GTAGAAGATG | CAGTAAAAGC | CATCTTAAAC | CAAAAGATTG | AGCCCT | | 166 |